(12) United States Patent
Rock et al.

(10) Patent No.: US 12,311,166 B2
(45) Date of Patent: May 27, 2025

(54) IMPLANTABLE MEDICAL SYSTEM

(71) Applicant: Medtronic, Inc., Minneapolis, MN (US)

(72) Inventors: Kaileigh E. Rock, Saint Paul, MN (US); Jason D. Hamack, Ramsey, MN (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 17/453,044

(22) Filed: Nov. 1, 2021

(65) Prior Publication Data

US 2022/0134092 A1    May 5, 2022

Related U.S. Application Data

(60) Provisional application No. 63/110,007, filed on Nov. 5, 2020.

(51) Int. Cl.
*A61N 1/05* (2006.01)
*A61B 17/00* (2006.01)

(52) U.S. Cl.
CPC ...... *A61N 1/0573* (2013.01); *A61B 17/00234* (2013.01); *A61B 2017/00243* (2013.01); *A61B 2017/00292* (2013.01); *A61N 2001/058* (2013.01)

(58) Field of Classification Search
CPC .... A61B 17/00234; A61B 2017/00243; A61B 2017/00292; A61N 1/057; A61N 1/0573; A61N 1/37205; A61N 1/37516; A61N 1/37518; A61N 1/3756; A61N 2001/058
See application file for complete search history.

(56) References Cited

U.S. PATENT DOCUMENTS

| | | | |
|---|---|---|---|
| 5,772,693 | A | 6/1998 | Brownlee |
| 6,289,251 | B1 | 9/2001 | Huepenbecker et al. |
| 6,370,434 | B1 | 4/2002 | Zhang et al. |
| 6,556,873 | B1 | 4/2003 | Smits |

(Continued)

FOREIGN PATENT DOCUMENTS

| | | |
|---|---|---|
| WO | 2016/126465 A1 | 8/2016 |
| WO | 2016/172106 A1 | 10/2016 |

OTHER PUBLICATIONS

International Search Report and Written Opinion of International Application No. PCT/US2021/057957, dated Mar. 1, 2022, 13 pp.

(Continued)

*Primary Examiner* — Mohamed G Gabr
(74) *Attorney, Agent, or Firm* — Shumaker & Sieffert, P.A.

(57) ABSTRACT

A medical system including a device head configured to be positioned in an atrium of a heart, an implantable medical device configured to be positioned within a vena cava of the heart, and a lead extending from the device head to the implantable medical device. A fixation element coupled to the device head is configured to engage tissues within the atrium. The device head includes an electrode configured to deliver therapy and/or sensing signals to tissues within the atrium using stimulation signals received from processing circuitry within the implantable medical device. The medical system may include a delivery catheter configured to allow delivery of the device head to the atrium.

18 Claims, 11 Drawing Sheets

(56) References Cited

U.S. PATENT DOCUMENTS

| | | | |
|---|---|---|---|
| 6,718,211 B2 | 4/2004 | Smits | |
| 7,801,622 B2 | 9/2010 | Camps et al. | |
| 8,548,605 B2 | 10/2013 | Ollivier | |
| 9,717,902 B2 | 8/2017 | Ollivier | |
| 10,350,416 B2 | 7/2019 | Bonner et al. | |
| 2003/0105501 A1 | 6/2003 | Warman et al. | |
| 2007/0179550 A1* | 8/2007 | Dennis | A61N 1/372 |
| | | | 607/36 |
| 2008/0269716 A1* | 10/2008 | Bonde | A61B 17/3468 |
| | | | 607/118 |
| 2018/0353751 A1 | 12/2018 | Pedersen et al. | |

OTHER PUBLICATIONS

Bar-Cohen et al., "Minimally Invasive Implantation of a Micropacemaker Into the Pericardial Space", American Heart Association, Inc., Circluation: Arrhythmia and Electrophysiology, Jul. 2018, 9 pp.

* cited by examiner

IMPLANTABLE MEDICAL SYSTEM

This application claims the benefit of U.S. Provisional Patent Application Ser. No. 63/110,007 (filed Nov. 5, 2020), which is entitled, "IMPLANTABLE MEDICAL SYSTEM" and is incorporated by reference herein in its entirety.

TECHNICAL FIELD

This disclosure is related to implantable medical systems.

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach, endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads, e.g., distal portions of elongated implantable medical leads, may be implanted at target locations selected to detect a physiological condition of the patient and/or deliver one or more therapies. For example, implantable medical leads may be delivered to locations within an atrium or ventricle to sense intrinsic cardiac signals and deliver pacing or antitachyarrhythmia shock therapy from a medical device coupled to the lead. In other examples, implantable medical leads may be tunneled to locations adjacent a spinal cord or other nerves for delivering pain therapy from a medical device coupled to the lead. Implantable medical leads may include anchoring components to secure a distal end of the lead at the target location.

Some cardiac pacemakers are sized to be completely implanted within one of the chambers of the heart, and may include electrodes integrated with or attached to the device housing rather than leads. Such cardiac pacemakers may include anchoring components to secure the pacemaker to cardiac tissue at a target location. Some cardiac pacemakers provide dual chamber functionality, by sensing and/or stimulating the activity of both atria and ventricles, or other multi-chamber functionality. A cardiac pacemaker may provide multi-chamber functionality via leads that extend to respective heart chambers, or multiple cardiac pacemakers may provide multi-chamber functionality by being implanted in respective chambers.

SUMMARY

In an example, a medical system comprises: an implantable medical device having a proximal end and a distal end, wherein the implantable medical device is configured to be positioned within a vena cava of a heart; a flexible lead, wherein a proximal end of the flexible lead is attached to the distal end of the implantable medical device, wherein the flexible lead is configured to extend from the vena cava to an atrium of a heart; a device head, wherein a first side of the device head is attached to a distal end of the flexible lead, wherein the device head is configured to be positioned within the atrium of the heart; a fixation element attached to the device head, wherein the fixation element is configured to engage tissue to substantially secure the device head within the atrium of the heart; and an electrode coupled to the device head, wherein the electrode is configured to provide stimulation to tissues of the heart when the device head is positioned within the atrium of the heart.

In an example, a system comprises: a medical assembly comprising: an implantable medical device having a proximal end and a distal end, wherein the implantable medical device is configured to be positioned within a vena cava of a heart; a flexible lead, wherein a proximal end of the flexible lead is attached to the distal end of the implantable medical device, wherein the flexible lead is configured to extend from the vena cava to an atrium of a heart; a device head, wherein a first side of the device head is attached to a distal end of the flexible lead, wherein the device head is configured to be positioned within the atrium of the heart; a fixation element attached to the device head, wherein the fixation element is configured to engage tissue to substantially secure the device head within the atrium of the heart; and an electrode coupled to the device head, wherein the electrode is configured to provide stimulation to tissues of the heart when the device head is positioned within the atrium of the heart; and a delivery catheter defining a lumen and defining a lumen opening at a distal end of the delivery catheter, wherein: the lumen is configured to surround at least the implantable medical device, the flexible lead, the device head, and the fixation element, and the fixation element, the device head, the flexible lead, and the implantable medical device are configured to pass distally through the lumen opening.

In an example, a technique comprises: positioning a device head, an electrode attached to the device head, and a fixation element attached to the device head within an atrium of a heart by transmitting an axial force to the device head; causing a flexible lead attached to the device head and attached to an implantable medical device to extend from the atrium of the heart to a vena cava of the heart using the transmitted axial force; and positioning the implantable medical device within the vena cava of the heart using the transmitted axial force.

The details of one or more examples are set forth in the accompanying drawings and the description below. Other features, objects, and advantages will be apparent from the description and drawings, and from the claims.

DETAILED DESCRIPTION

Figure 1:
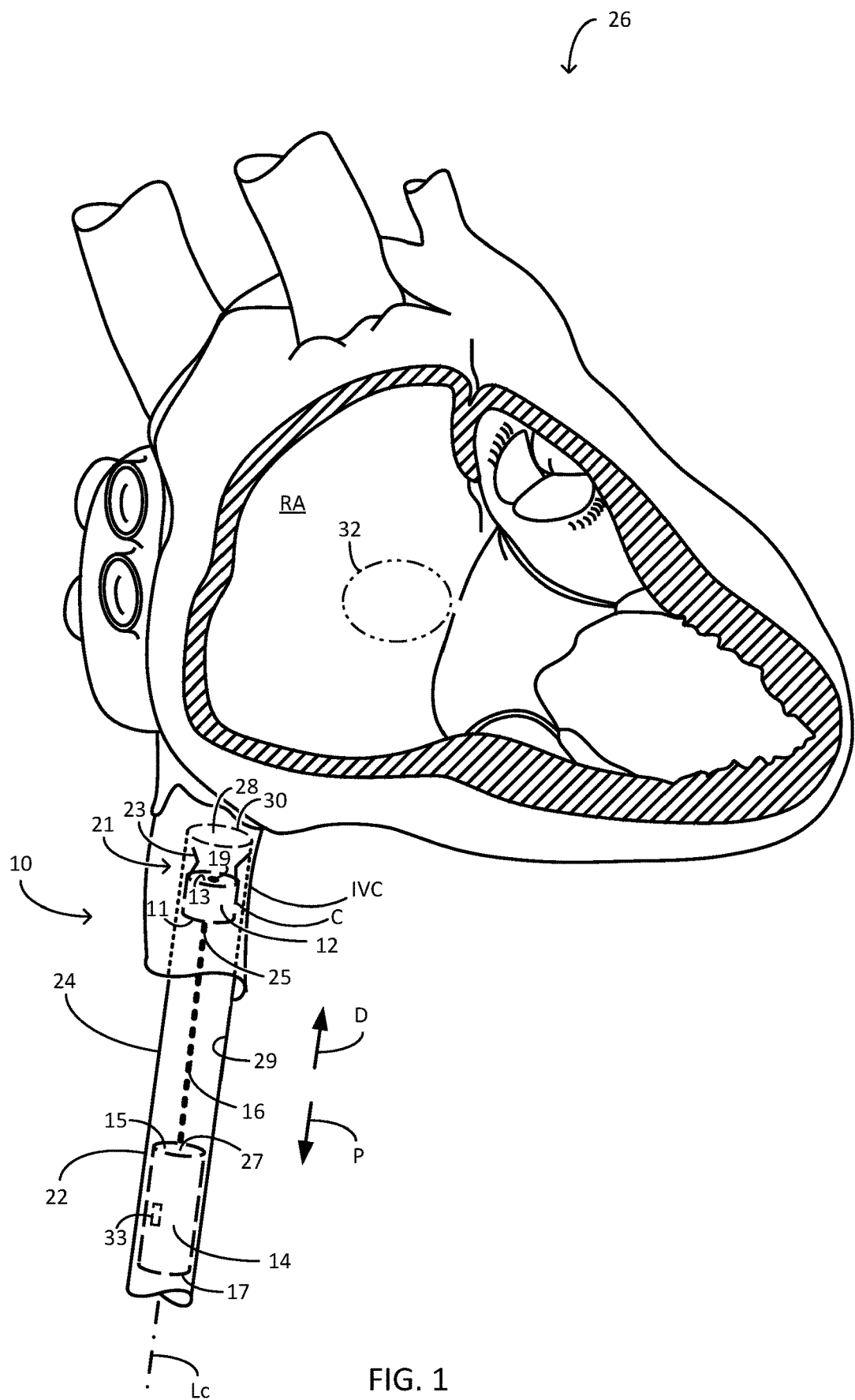
FIG. 1 is a conceptual diagram illustrating an example medical system and delivery catheter.

This disclosure describes a medical system configured to position one or more electrodes within a chamber of a heart. The medical system includes a device head configured to be positioned within the atrium and an implantable medical device ("IMD") configured to be positioned within a vena cava leading to the atrium. A flexible lead extends between the device head and the IMD. The IMD includes therapy delivery circuitry configured to provide stimulation signals via the flexible lead to the one or more electrodes of the device head. The flexible lead is configured to allow the device head to engage tissue within the atrium (e.g., in the triangle of Koch region or another location) as the IMD is positioned within the vena cava. In examples, the lead is configured to allow the device head to engage tissues within a right atrium of a heart as the IMD is positioned within inferior vena cava (IVC) of the heart. Positioning the IMD within the vena cava may improve spacing constraints compared to systems configured for positioning an IMD within the atrium itself. For example, positioning within the vena cava may allow the IMD to be larger, which may allow increased battery capacity, circuit complexity, and/or other improvements compared to IMDs configured for positioning within an atrium of a heart.

The lead extending between the device head and the IMD is configured to exhibit sufficient flexibility to allow a clinician to position the device head at a desired target site (e.g., The triangle of Koch region, or another target site on the atrial tissue) as the IMD remains positioned substantially within the vena cava (e.g., within the IVC). For example, a body of the device head may define an axis ("head axis") while the body of the IMD defines a separate axis ("IMD axis"). The lead may be configured to exhibit a flexibility allowing the head axis to substantially maintain a plurality of orientations relative to the IMD axis, such that the device head may be maneuvered toward a target site within the atrium as the IMD remains substantially within the vena cava. In examples, the lead exhibits sufficient flexibility to extend between an IMD in an IVC to a device head positioned to place an electrode in proximity to (e.g., in contact with) a target site within a triangle of Koch region. The lead may be sufficiently flexible to allow a plurality of relative orientations between the head axis and the IMD axis as the device head is caused (e.g., by a clinician) to negotiate a path from a vena cava to a target site in the atrium (e.g., a target site in the triangle of Koch region).

The medical system may be configured to substantially maintain the one or more electrodes of device head in close proximity to a target site within the atrium as the IMD remains substantially within the vena cava. In examples, a fixation element configured to engage tissue is attached to the device head. The fixation element may be configured to engage tissue (e.g., atrial tissue) to secure the device head and IMD to tissue and to place the one or more electrodes of the device head in a desired engagement with tissue at the target site (e.g., in an atrium). The fixation element may include, for example, one or more fixation tines configured to extend distally from the device head. The one or more electrodes are configured to receive stimulation signals from the IMD and deliver sensing/therapy signals to the tissue based on the stimulation signals. In examples, the one or more electrodes include a shallow electrode configured to deliver sensing/therapy signals to tissue (e.g., atrial tissue) in a substantially non-invasive manner. In examples, the one or more electrodes may include a deep electrode configured to be advanced into the tissue for sensing signal from and the delivery of therapy signals to tissue such as ventricular tissue, or tissue of the His-Purkinje conduction system. The device head may include one or more shallow electrodes, one or more deep electrodes, and/or a combination of shallow electrodes and deep electrodes. The medical system may include one or more return electrodes configured to be used with the shallow electrode and/or deep electrode for sensing and/or delivery of therapy. In some examples, the medical system may include an IMD fixation device configured to engage tissue to substantially maintain the IMD within the vena cava.

In examples, the medical system includes a delivery catheter defining a lumen configured to allow passage of the IMD, the lead, and the device head therethrough. The catheter may be configured to deliver the medical system intravenously through the vena cava. In examples, the catheter includes a proximal section and a distal section. The distal section may be configured to extend into the atrium (e.g., a right atrium) as the proximal section remains substantially within the vena cava (e.g., an IVC). The distal section may be configured to define a curvature relative to the proximal section when the distal section is in a substantially relaxed configuration (e.g., in the substantial absence of external forces acting on the distal section). In examples, the distal section includes a shape memory alloy configured to cause the distal section of define the curvature. In some examples, the distal section is configured to define a first curvature and define a second curvature out of plane with the first curvature in order to, for example, cause the lumen to define a path from a vena cave to a target site within an atrium. For example, the distal section may be configured to cause the lumen to define a path from an IVC to a target site within the triangle of Koch region of a right atrium. In examples, the device head defines a shape (e.g., an outer perimeter) configured to mechanically engage with an inner surface of the catheter lumen as the device head passes through the catheter lumen, The device head may be configured to mechanically engage the inner surface to substantially maintain the device head in an orientation whereby the fixation mechanism of the device head substantially faces a lumen opening defined by the distal portion of the catheter.

The delivery catheter defines a distal opening into the lumen at a distal end of the delivery catheter. The device head, the lead, and the IMD are configured to translate (e.g., slidably translate) within the lumen and through the distal opening. Hence, the delivery catheter may be configured to define a path from a vena cava to a target site to position the device head, the lead, and the 1 MB. In examples, the lead extending between the device head and the IMD has a sufficient axial stiffness such that a force (e.g., a pushing and/or pulling force) imparted to the IMD (e.g., by a stylet) causes the lead to transmit at least some portion of the imparted force to the device head, causing movement of the 1 MB, the lead, and the device head through the lumen of the delivery catheter. In examples, the lead has a sufficient axial stiffness such that that a force (e.g., a pushing and/or pulling force) imparted to the device head (e.g., by a stylet) causes the lead to transmit at least some portion of the imparted force to the 1 MB, causing movement of the IMD, the lead, and the device head through the lumen of the delivery catheter.

FIG. 1 is a conceptual diagram illustrating an example medical system 10. Medical system 10 includes a device head 12, an implantable medical device 14 ("IMD 14"), and a lead 16 extending between device head 12 and IMD 14. In FIG. 1, device head 12, IMD 14, and lead 16 are positioned within a lumen 20 defined by delivery catheter 18 and shown with hidden lines. Delivery catheter 18 is configured to define a pathway through lumen 20 substantially from a vena cava of heart 26 (e.g., the IVC) to a chamber of heart 26 (e.g., the RA). Device head 12, lead 16, and IMD 14 are configured to be translated through lumen 20 to position device head 12 in proximity to a target site 32 within the chamber of heart 26 (e.g., the RA) as IMD 14 remains substantially within a vena cava of heart 26 (e.g., the IVC). Although the examples herein discuss delivery and placement of IMD 14 within the RA of heart 26, medical system 10 may be configured to position IMD 14 in other chambers of heart 26 in a like manner as that described for the RA of heart 26.

Device head 12, lead 16, and IMD 14 may be configured to translate collectively through lumen 20 in the distal direction D and/or the proximal direction P. For example, device head 12, lead 16, and IMD 14 may be configured such that a force on device head 12 or IMD 14 causes motion of both device head 12 and IMD 14 through lumen 20. In examples, IMD 14 includes a distal end 15 ("IMD distal end 15") and a proximal end 17 ("IMD proximal end 17"). Device head 12 may include a first side 11 ("head first side 11") and a second side 13 ("head second side 13") opposite head first side 11. Lead 16 may be coupled to IMD distal end 15 and head first side 11. In other examples, lead 16 may be coupled to other portions of IMD 14 and/or device head 12 to extend between IMD 14 and device head 12.

An electrode 19 is coupled to device head 12. Electrode 19 is electrically connected to circuitry within IMD 14 via lead 16, and thereby configured to receive stimulation signals from IMD 14 for delivery to tissues (e.g., atrial tissue) of heart 26, as well as allow IMD 14 to sense electrical signals from heart 26. In examples, electrode 19 is coupled to head second side 13. In examples, as depicted in FIG. 1, electrode 19 is a shallow electrode configured for sensing and delivery of therapy signals to tissue in a substantially non-invasive manner. In other examples, electrode 19 may be a deep electrode configured to penetrate the tissues for sensing and delivery of therapy signals. Medical system 10 may include any number of electrodes in any configuration, including one or more electrodes supported by device head 12, IMD 14, and/or lead 16.

A fixation element 21 configured to engage tissue is attached to device head 12. Fixation element 21 may include, for example, one or more elongated tines such as fixation tine 23 configured to substantially maintain an orientation of device head 12 with respect to target site 32. Fixation element 21 may include fixation tines of any shape, including helically-shaped fixation tines. Fixation element 21 (e.g., fixation tine 23) may be configured to penetrate tissue in the vicinity of target site 32 to substantially maintain the orientation. In examples, fixation element 21 is configured to substantially maintain an orientation of electrode 19 with respect to target site 32 when fixation element 21 engages tissue. In examples, fixation element 21 may be configured to substantially maintain contact between electrode 19 and tissues within target site 32 when fixation element 21 engages the tissue.

Lead 16 extends between device head 12 and IMD 14. As will be discussed, lead 16 is configured to extend between device head 12 and IMD 14 when device head 12 is positioned substantially within an atrium of heart 26 (e.g., the RA) and IMD 14 is positioned substantially within a vena cava of heart 26 (e.g., the IVC). Lead 16 may be a flexible lead configured to accommodate curvatures necessary when IMD 14 is positioned substantially within a vena cava of heart 26 and device head 12 is positioned substantially within an atrium of heart 26. In examples, a distal end 25 of lead 16 ("lead distal end 25") may be coupled to device head 12. A proximal end 27 of lead 16 ("lead proximal end 27") may be coupled to IMD 14. In examples, lead 16 is coupled to IMD distal end 15 and head first side 11. Lead 16 may be configured to enable transmission of stimulation signals from circuitry of IMD 14 to electrode 19 and/or sensing signals from electrode 19 to circuitry of IMD 14. Lead 16 may include an electrical conductor configured to transmit the stimulation signals and/or sensing signals.

Lead 16 may be configured to cause movement of medical system 10 when a force (e.g., in the distal direction D and/or proximal direction P) is exerted on IMD 14 and/or device head 12. Lead 16 may be configured to transmit a force exerted on one of IMD 14 or device head 12 (e.g., in the distal direction D or proximal direction P) to the other of IMD 14 or device head 12. For example, lead 16 may be configured such that a when IMD 14 exerts a force in the distal direction D or proximal direction P on lead proximal end 27, lead distal end 25 exerts a force in the same direction on device head 12. Lead 16 may be configured such that when device head 12 exerts a force in the distal direction D or proximal direction P on lead distal end 25, lead proximal end 27 exerts a force in the same direction on IMD 14.

In examples, lead 16 defines a lead axis from lead proximal end 27 to lead distal end 25. The lead axis may linear, curved, and/or curvilinear. Lead 16 may be configured to exhibit a bending moment about the lead axis, such that lead 16 may transmit an axial force (e.g., between IMD 14 and device head 12) as lead 16 accommodates any curvatures necessary to extend between device head 12 and IMD 14. Lead 16 may be configured to transmit a force exerted on one of IMD 14 or device head 12 to the other of IMD 14 or device head 12 when lead axis is substantially linear, curved, and/or curvilinear.

Delivery catheter 18 defines lumen 20 extending through a proximal section 22 ("catheter proximal section 22") and a distal section 24 ("catheter distal section 24"). Lumen 20 extends through catheter proximal section 22 and catheter distal section 24 to a lumen opening 28 defined at a distal end 30 of delivery catheter 18 ("catheter distal end 30"). An inner wall 29 of delivery catheter 18 may define lumen 20 and lumen opening 28. Delivery catheter 18 may define an axis Lc extending through lumen 20 and lumen opening 28. Delivery catheter axis Lc may be substantially linear, curved, and/or curvilinear.

Delivery catheter 18 may be configured to allow a clinician to deliver medical system 10 through a vena cava (e.g., the IVC) for implantation of device head 12 within an atrium (e.g., the RA) of heart 26. Delivery catheter 18 may be intravenously transited through the IVC such that catheter distal section 24 passes into the RA. Delivery catheter 18 may be configured to substantially deliver medical system 10 (e.g., device head 12) to the target site 32. In examples, delivery catheter 18 is configured to allow the clinician to position catheter distal end 30 in proximity to a target site 32 as catheter distal section 24 transitions from the vena cava (e.g., the IVC) into the atrium (e.g., RA). Target site 32 may include an appendage or triangle of Koch region of the RA, or some other portion of heart 26, or other locations within a body of a patient. In examples, delivery catheter 18 is configured to substantially position catheter distal end 30 such that lumen opening 28 substantially faces target site 32 (e.g., such that a vector normal to lumen opening 28 intersects target site 32). In examples, catheter distal section 24 is configured to position lumen opening 28 in proximity to target site 32 in an atrium of heart 26 (e.g., the RA) when catheter distal section 24 substantially resides in a vena cava of heart 26 (e.g., the IVC).

Device head 12, IMD 14, and lead 16 may be positioned within any portion of lumen 20. In examples, device head 12 and at least a portion of lead 16 are configured to reside within catheter distal section 24 as catheter distal end 30 is positioned in the proximity of target site 32. In examples, IMD 14 is configured to reside within catheter proximal section 22 as catheter distal end 30 is positioned in the proximity of target site 32. In some examples, lead 16 is configured to extend from catheter distal section 24 to catheter proximal section 22 as catheter distal end 30 is positioned in the proximity of target site 32. In some examples, device head 12, IMD 14, and lead 16 are configured to reside outside of delivery catheter 18 as catheter distal end 30 is positioned in the proximity of target site 32, and configured to be inserted into lumen 20 at a proximal end of delivery catheter 18 when catheter distal end 30 is positioned in the proximity of target site 32. Device head 12, IMD 14, and lead 16 are configured to be translatable through at least some portion of lumen 20 when catheter distal end 30 is positioned in the proximity of target site 32. In examples, device head 12 defines a shape (e.g., an outer perimeter C) configured to mechanically engage with an inner surface defining lumen 20 as device head 12 passes through the lumen 20. Device head 12 may be configured to mechanically engage the inner surface to substantially maintain device head 12 in an orientation whereby second side 13 substantially faces lumen opening 28 as device head 12 translates through delivery catheter 18.

Figure 2:
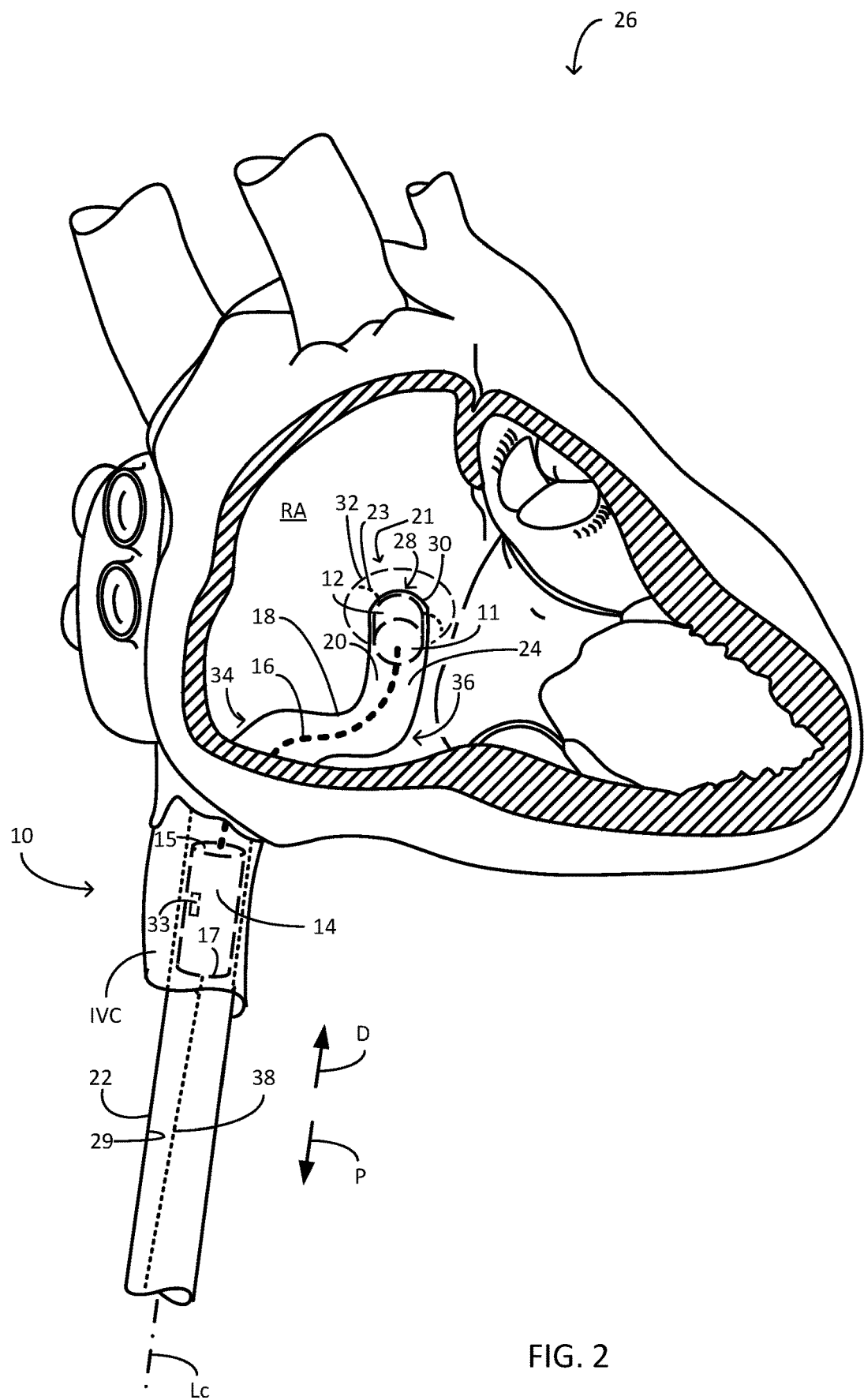
FIG. 2 is a conceptual diagram illustrating the medical system of FIG. 1 translated through the delivery catheter of FIG. 1.

FIG. 2 is a conceptual diagram illustrating delivery catheter 18 having positioned catheter distal end 30 in the proximity of target site 32. Medical system 10 is positioned within delivery catheter 18 such that device head 12 is positioned substantially at or near lumen opening 28. Device head 12 and some portion of lead 16 are within catheter distal section 24 while IMD 14 is substantially within catheter distal section 24. Medical system 10 may be caused to translate as delivery catheter 18 translates using, for example, a force on medical system 10 exerted by an elongated member 38 (e.g., a stylet) extending within lumen 20 of delivery catheter 18. In FIG. 2, catheter proximal section 22 is substantially within a vena cava (e.g., the IVC) of a heart 26. Catheter distal section 24 is substantially within an atrium (e.g. the RA) of heart 26.

Delivery catheter 18 may be configured to position in the atrium such that lumen opening 28 substantially faces target site 32. Target site 32 may be, for example, an area within the triangle of Koch region of heart 26, or some other target area within heart 26. In examples, delivery catheter 18 defines a first curvature 34 and/or a second curvature 36, in order to assist the clinician in positioning catheter distal end 30 in the proximity of target site 32. Delivery catheter 18 (e.g., catheter distal section 24) may define the first curvature 34 and/or second curvature 36 when catheter distal section 24 is in a substantially relaxed configuration (e.g., in the substantial absence of external forces acting on distal section 24). In examples, first curvature 34 and/or second curvature 36 are configured to substantially define a pathway through lumen 20 from the IVC (e.g., from the inferior end of the IVC) to target site 32 in the RA of heart 26. Delivery catheter 18 may be configured such that first curvature 34 defines a curvature in a first plane (e.g., a first Euclidean plane) and second curvature 36 defines a curvature in a second plane (e.g., a second Euclidean plane). The first plane and the second plane may define an angle between the first plane and the second plane when delivery catheter 18 defines first curvature 34 and second curvature 36, such that first curvature 34 and second curvature 36 are out-of-plane with one another. In examples, delivery catheter 18 may be configured to allow a clinician to establish contact between a portion of catheter distal section 24 defining lumen opening 28 and tissues (e.g., atrial tissue) within target site 32.

In examples, IMD 14 is configured to receive a force in the distal direction D (e.g., a pushing force) to cause medical system 10 to translate through lumen 20 in the distal direction D. IMD 14 may be configured to receive a force in the proximal direction P (e.g., a pulling force) and cause medical system 10 to translate through lumen 20 in the proximal direction P. IMD 14 may be configured to engage elongated member 38 (e.g., a stylet) to receive the force in the distal direction D and/or proximal direction P to, for example, cause medical system 10 (e.g., IMD 14, lead 16, and device head 12) to move in the same direction as the received force. In some examples, device head 12 is configured to receive a force (e.g., from a stylet) in the distal direction D (e.g., a pushing force) and/or proximal direction P (e.g., a pulling force) to cause medical system 10 to translate through lumen 20 in the direction of the exerted force.

Thus, delivery catheter 18 may be configured to substantially guide device head 12 toward or away from catheter distal end 30 when a force is exerted on medical system 10 (e.g., on IMD 14 and/or device head 12). Delivery catheter 18 may be configured to substantially provide a pathway through lumen 20 to catheter distal end 30 for the translation of medical system 10, such that a clinician may cause medical system 10 (e.g., device head 12) to position at or near lumen opening 28 by exerting the force in the distal direction on medical system 10.

Delivery catheter 18 defines lumen opening 28 such that device head 12, fixation element 21, electrode 19, lead 16, and IMD 14 may pass therethrough. Fixation element 21 may be configured to engage tissue within target site 32 as fixation element 21 passes through lumen opening 28. In examples, fixation element 21 (e.g., fixation tine 23) is configured to extend distally from device head 12 as medical system 10 translates distally through catheter distal section 24. Fixation element 21 may be configured to penetrate tissues within target site 32 as fixation element 21 passes through lumen opening 28 in order to engage the tissues. For example, a portion of fixation element 21 (e.g., fixation tine 23) may be resiliently biased to expand outward as fixation element 21 passes through lumen opening 28, in order to aid in grasping the tissue. Delivery catheter 18 may be configured to radially constrain fixation element 21 (e.g., fixation tine 23) as device head 12 translates within delivery catheter 18 toward or away from lumen opening 28.

Catheter distal section 24 is configured to maintain device head 12 in an orientation such that some portion of fixation element 21 (e.g., a free end of fixation tine 23) passes through lumen opening 28 before device head 12 passes through lumen opening 28. For example, when fixation elements 21 (e.g., fixation tine 23) extends distally from head second side 13, catheter distal section 24 may be configured such that head second side 13 substantially faces lumen opening 28 and head first side 11 substantially faces away from lumen opening 28 as device head 12 translates within catheter distal section 24 toward lumen opening 28. Hence, catheter distal section 24 and medical system 10 may be configured such that fixation element 21 engages tissues at target site 32 when catheter distal section 24 guides medical system 10 (e.g., device head 12) toward lumen opening 28 substantially facing target site 32. Additionally, with lumen opening 28 configured to allow with device head 12, lead 16, and IMD 14 to pass therethrough, delivery catheter 18 may be withdrawn proximally from the atrium and the vena cava as device head 12 substantially remain in the atrium (e.g., the RA), and IMD 14 remain substantially with the vena cava (e.g., the IVC). Delivery catheter 18 may be configured to substantially straighten when proximally withdrawn to, for example, allow device head 12, lead 16, and IMD 14 to pass through lumen opening 28. For example, catheter distal section 24 may be configured to reduce and or substantially eliminate a curvature of first curvature 34 and/or second curvature 36 to, for example, allow passage of catheter distal section 24 over IMD 114.

Figure 3:
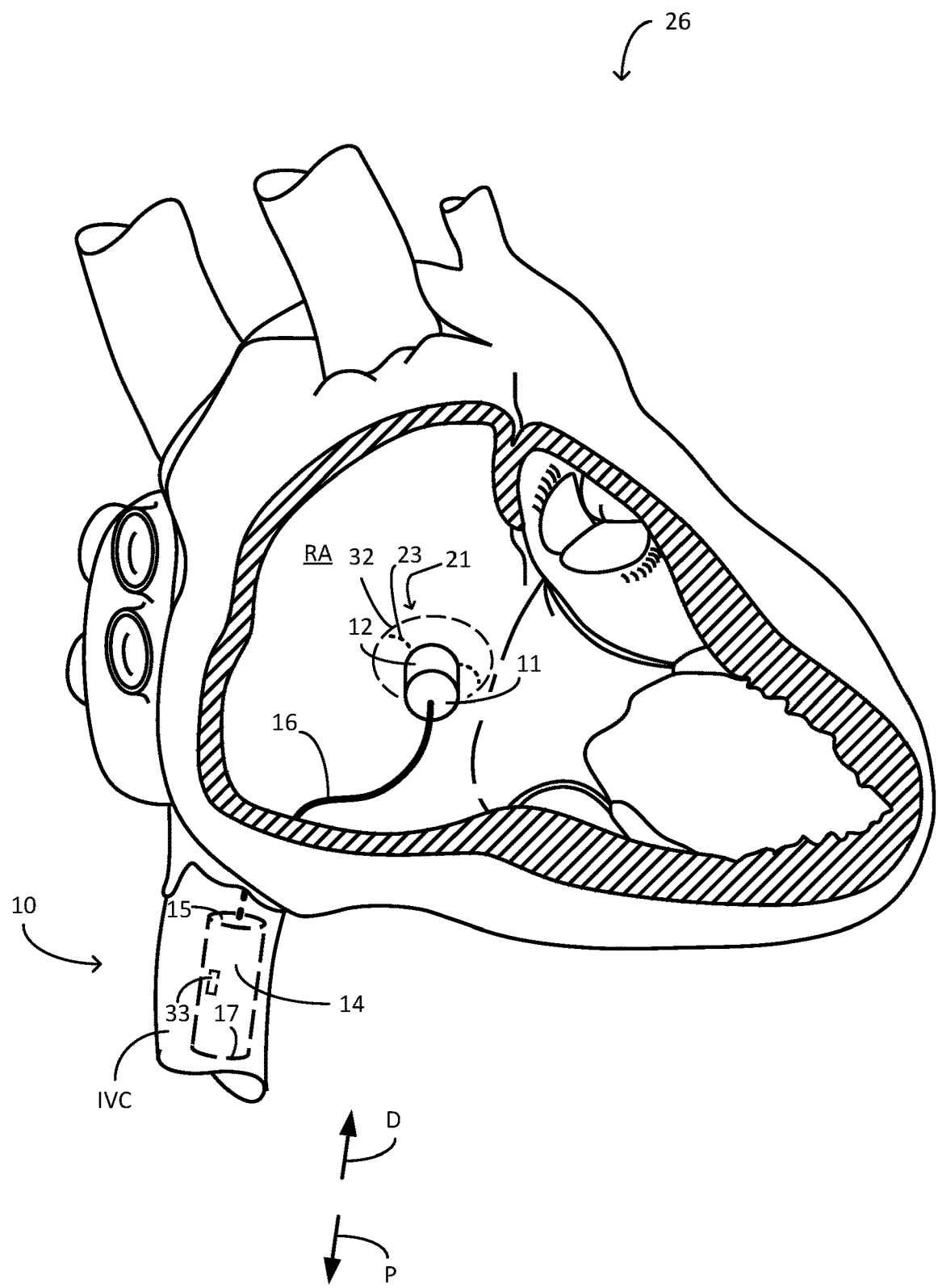
FIG. 3 is a conceptual diagram illustrating the medical system of FIG. 1 positioned with a heart.

FIG. 3 is a conceptual diagram illustrating device head 12 within the RA of heart 26 as IMD 14 resides substantially within the IVC of heart 26. Delivery catheter 18 has been proximally withdrawn from the RA and IVC. Fixation element 21 (e.g., fixation tine 23) is grasping tissues within target site 32 to substantially maintain device head 12 within the RA. Lead 16 extends between device head 12 and IMD 14 substantially within the IVC. Medical system 10 is configured such that IMD 14 may transmit stimulation signals to an electrode (e.g., electrode 19 (FIG. 1)) coupled to device head 12. Fixation element 21 causes device head 12 to substantially maintain a position whereby the electrode may deliver therapy signals to tissues within target site 32 based on the stimulation signals received from IMD 14 via lead 16, and IMD 14 may sense signals from the tissues via the electrode. In examples, medical system 10 includes an IMD fixation device 33 configured to engage tissue to substantially maintain IMD 14 within the vena cava when device 12 positions in the RA (or another chamber of the heart). Fixation device 33 may include, for example, one or more resiliently biased members configured to expand outward when delivery catheter 18 is withdrawn proximally, a mechanism (e.g., a wire or other mechanism) configured to be operated by a clinician to cause fixation device 33 to engage the tissue, or some other structure sufficient to engage tissue to substantially maintain IMD 114 within the vena cava.

Figure 4:
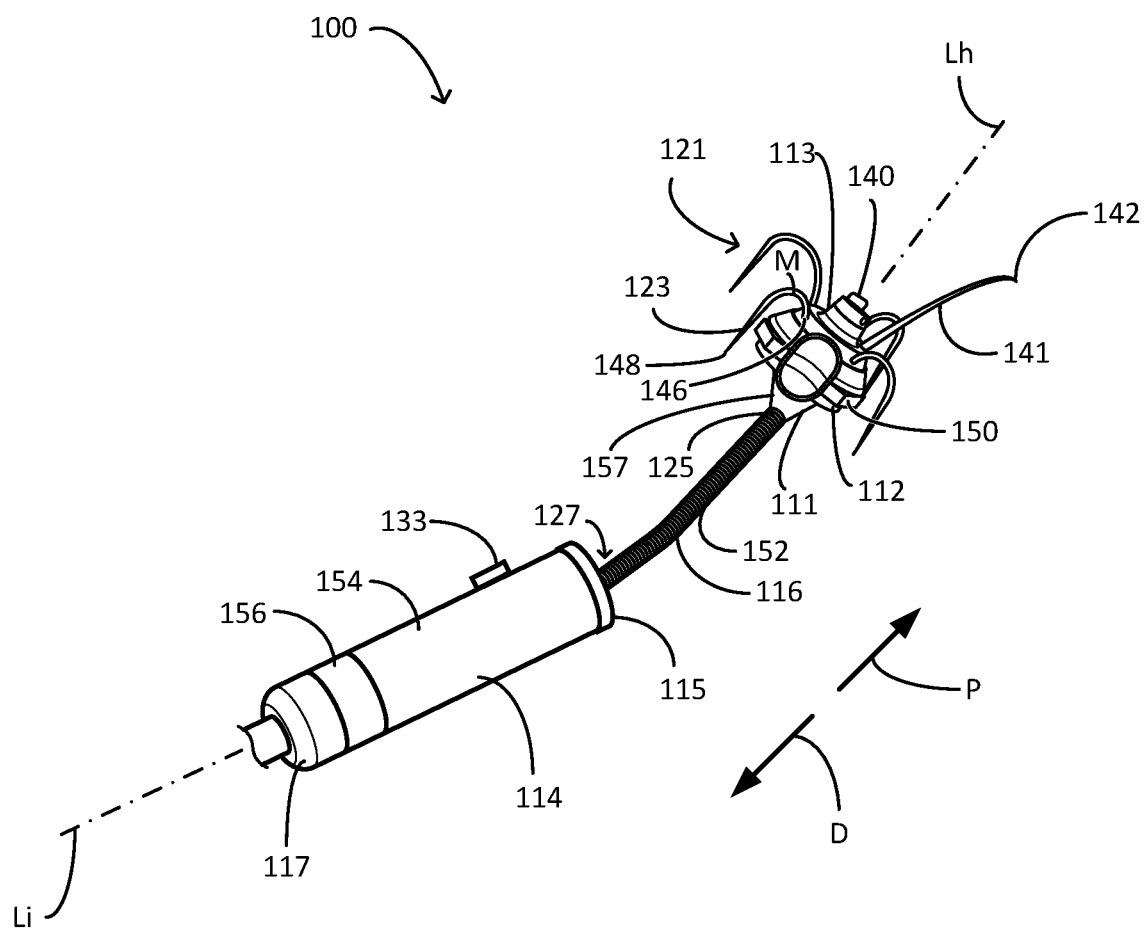
FIG. 4 is a conceptual diagram of an example medical system including a device head, a lead, and an implantable medical device.

FIG. 4 illustrates an example medical system 100. Medical system 100 is an example of medical system 10. Medical system 100 includes device head 112 including head first side 111 and head second side 113, IMD 114 including IMD distal end 115 and IMD proximal end 117, lead 116 including lead distal end 125 and lead proximal end 127, fixation element 121 including fixation tine 123, and IMD fixation device 133, all of which may be configured individually and in relation to each other in the same manner as that discussed for the like-named components of medical system 10. In FIG. 4, device head 112 defines an axis Lh intersecting head first side 111 and head second side 113. IMD 114 define an axis Li intersecting IMD distal end 115 and IMD proximal end 117.

Medical system 100 may include one or more electrodes configured to deliver low-voltage electrical pulses to the heart or sense a cardiac electrical activity, e.g., depolarization and repolarization of the heart. The one or more electrodes may be coupled to device 112. For example, in FIG. 4, shallow electrode 140 and deep electrode 142 are coupled to second side 113 of device head 112. Shallow electrode 140 and/or deep electrode 142 may be examples of electrode 19 (FIG. 1). Shallow electrode 140 may be configured to deliver sensing/therapy signals to tissue in a substantially non-invasive manner. In examples, shallow electrode 140 is an atrial electrode. Deep electrode 142 may be configured to be advanced into tissue for the delivery of sensing/therapy signals. In some examples, deep electrode 142 is supported by an electrode support member 141 extending distally from device head 112. Electrode support member 141 and/or deep electrode 142 may be configured to penetrate tissues to substantially implant deep electrode 142 within the tissues (e.g., to target the His bundle (HB), right bundle branch (RBB), left bundle branch (LBB), or other ventricular tissue). Shallow electrode 140 and/or deep electrode 142 may be configured to receive stimulations signals from processing circuitry within IMD 114. Shallow electrode 140 and/or deep electrode 142 may be any of a number of different types of electrodes, including button electrodes, pad electrodes, helical electrodes, tine electrodes, or the like.

Fixation element 121 may be configured to engage tissue and substantially maintain an orientation of device head 112 relative to the tissue. Fixation element 121 includes one or more elongated tines such as fixation tine 123. Fixation tine 123 is an example of fixation tine 23 (FIGS. 1-3). In general, a tine may refer to any structure that is capable of securing a lead or leadless implantable medical device to a location within the heart. In some examples, a tine (e.g. fixation tine 123 and/or electrode support member 141) may be composed of a shape-memory allow that allows deformation along the length of the tine. A tine may be substantially flat along the length of the tine. In other examples, a tine may substantially define a helix and/or helical member.

In examples, fixation tine 123 includes a fixed end 146 coupled to device head 112 and a free end 148 opposite fixed end 146. In examples, free end 148 is configured to penetrate tissue. Fixation tine 123 may be biased so that at least some portion of fixation tine 123 expands radially as fixation tine 123 passes through lumen opening 28 (FIG. 1). Fixation tine 123 may be biased to drive free end 148 radially outward from device head axis Lh as free end 148 passes through lumen opening 28. The biasing tending to drive free end 148 radially outward as fixation tine 123 extends through lumen opening 28 may cause fixation tine 123 to substantially grasp tissue and more securely anchor device head 112 within an atrium of heart 26. Free end 148 may pierce the tissue and may act to pull device head 112 and other portions of medical system 10 toward a target site (e.g., target site 32 (FIG. 1)) as fixation tine 123 elastically bends or curves radially outward. Fixation element 121 may include any number of fixation tines, which may be configured similarly to fixation tine 123.

The biasing of fixation tine 123 tending to drive free end 148 radially outward may cause fixation tine 123 to assume any general shape. In some examples, the biasing of fixation tine 123 tends to cause fixation tine 123 to position such that free end 148 establishes a position proximal to a midpoint M between fixed end 146 and free end 148 (e.g., as depicted at FIG. 4). In some examples, the biasing of fixation tine 123 tends to cause fixation tine 123 to position such that free end 148 remains distal to midpoint M between fixed end 146 and free end 148. Fixation tine 123 may be formed to have a preset shape and may be formed using any suitable material. In examples, fixation tine 123 comprises a nickel-titanium alloy such as Nitinol.

In some examples, fixation tine 123 may be configured to substantially maintain a delivery configuration where free end 148 is distal to fixed end 146 and distal to midpoint M (e.g., as depicted in FIG. 1). For example, fixation tine 123 may be configured to substantially maintain the delivery configuration when free end 148 is constrained from outward radial motion by inner wall 29 of delivery catheter 18 (FIGS. 1-2). Delivery catheter 18 may be configured to substantially maintain fixation tine 123 in the delivery configuration as device head 112 translates within lumen 20 of delivery catheter 18. Substantially maintaining free end 148 distal to midpoint M (e.g., in the delivery configuration) may facilitate the penetration of tissue by free end 148 when fixation tine 123 passes through lumen opening 28 of delivery catheter 18.

Device head 112 may be configured to limit its rotation when within a lumen defined by a delivery catheter (e.g., lumen 20 defined by delivery catheter 18 (FIGS. 1-2)). For example, device head 112 may be configured to limit its rotation such that head second side 113 remains distal to head first side 111 as device head 112 translates distally and/or proximally within lumen 20. In some examples, device head 112 is configured to maintain some portion of fixation element 121 distal to head second side 113 as device head 112 translates within lumen 20, in order to cause the portion of fixation element 121 to pass through lumen opening 28 before device head 112 passes through lumen opening 28. Substantially maintaining the portion of fixation element 121 distal to device head 112 as device head 112 translates distally toward lumen opening 28 (FIGS. 1-3) may assist in the engagement of fixation element 121 with tissues within target site 32 (FIGS. 1-3), such that fixation element 121 may substantially maintain an orientation of device head 112 with respect to target site 32.

In examples, device head 112 may define a dimension substantially perpendicular to device head axis Lh, with the dimension configured to cause some portion of device head 112 to engage an inner wall (e.g., inner wall 29) of the lumen, in order to limit the rotation of device head axis Lh relative to the inner wall. For example, device head 112 may define a dimension configured to limit a rotation of device head axis Lh relative to a portion of catheter axis Lc (FIGS. 1-2). Delivery head 112 may include one or more protrusions 150 extending radially outward from device head axis Lh and defining the dimension. Protrusion 150 may be configured to engage inner wall 29 of delivery catheter 18 (FIGS. 1-2) when device head 112 causes (or attempts to cause) rotation of device head axis Lh relative to catheter axis Lc. Device head 112 may include any number of protrusions 150, and protrusion 150 may define any geometry. In other examples, in addition to or instead of protrusion 150, device head 112 may define a substantially constant radius around device head axis Lh configured to limit a rotation of device head axis Lh relative to a delivery catheter axis Lc.

Lead 116 extends between device head 112 and IMD 114. In examples, lead distal end 125 is coupled to head first side 111 and lead proximal end 127 is coupled to IMD distal end 115. Lead 116 is configured to cause movement of distal head 112 and IMD 114 when a force in the distal direction D or proximal direction P is imparted to distal head 112 or IMD 114 (e.g., by stylet 38 (FIG. 2)). Lead 116 may be configured to transmit a distal and/or proximal force from IMD 114 to device head 112, and/or from device head 112 to IMD 114.

In examples, lead 116 is configured such that movement of head first side 111 causes movement of lead distal end 125, and vice-versa. In examples, lead 116 is configured such that movement of IMD distal end 115 causes movement of lead proximal end 127, and vice-versa. Lead 116 may be configured such that a movement of IMD 114 or device head 112 in the distal direction D causes the other of IMD 114 or device head 112 to move in the distal direction D. Lead 116 may be configured such that a movement of IMD 114 or device head 112 in the proximal direction P causes the other of IMD 114 or device head 112 to move in the proximal direction P. In examples, lead 116 is configured to transmit the force between IMD 114 and device head 112 at least partially through a lead axis running through lead 116 from lead proximal end 127 to lead distal end 125. Lead 116 may be configured to transmit the force when the lead axis defines a linear, curved, and/or curvilinear shape.

In examples, lead 116 is configured to substantially push device head 112 when lead 116 receives a distal force (e.g., a force in the distal direction D) from IMD 114. Lead 116 may be configured such that, when lead proximal end 127 receives the distal force from IMD 114, lead distal end 125 transmits some portion of the force to device head 112. Lead 116 may be configured to transmit the portion of the distal force to device head 112 when the lead axis defines one or more curvatures, such as when lead 116 extends through one or more of first curvature 34 and/or second curvature 36 (FIGS. 1-2). In examples, lead 116 includes an outer lead body 152 configured to transmit the distal force to device head 112 when lead 116 defines the one or more curvatures. For example, outer lead body 152 may include a helical coil substantially surrounding some or all of the lead axis between lead proximal end 127 and lead distal end 125. In some examples, outer lead body 152 may be a substantially unitary body having one or more slits at least partially around a circumference of outer lead body and configured to allow bending of lead 116 while transferring a distal force from lead proximal end 127 to lead distal end 125. Outer lead body may have other configurations in other examples.

Lead 116 may be a flexible lead configured to allow positioning of device head 112 relative to IMD 114 in a variety of relative orientations. Lead 116 may be configured (e.g., have sufficient flexibility) to allow device head axis Lh to rotate and/or translate relative to IMD axis Li as device head 112 and IMD 114 translates through lumen 20 of delivery catheter 18 (FIGS. 1-2). In examples, lead 116 is configured to allow device head axis Lh and IMD axis Li to remain substantially parallel with catheter axis Lc (FIGS. 1-2) as device head 112 and IMD 114 translate through lumen 20 of delivery catheter 18. For example, lead 116 may be configured to allow device head axis Lh to remain substantially parallel with a portion of catheter axis Lc in catheter distal section 24 as device head 112 translates through catheter distal section 24 (e.g., through portions defining first curvature 34 and/or second curvature 36 (FIGS. 1-2)). Lead 116 may be configured to allow IMD axis Li to remain substantially parallel with a portion of catheter axis Lc in catheter proximal portion 24 as device head 112 translates through catheter distal section 24.

In examples, lead 116 is configured to extend between device head 112 and IMD 114 when fixation element 121 engages tissue within an atrium (e.g., the RA) of heart 26 and IMD 114 is positioned substantially within a vena cava (e.g., the IVC) of heart 26. Lead 116 may be configured to have sufficient flexibility to extend between device head 112 and IMD 114 when device head axis Lh and IMD axis Li define skew lines (e.g., non-intersecting and non-parallel lines), substantially parallel lines, and/or intersecting lines. Lead 116 may be configured to have sufficient flexibility such that the lead axis of lead 116 may define one or more curvatures relative to IMD axis Li and/or device head axis Lh. In examples, lead 116 may be configured to define a primary curvature and a secondary curvature, with the primary curvature defining a curvature in a primary plane (e.g., a primary Euclidean plane) and the secondary curvature defining a curvature in a secondary plane (e.g., a secondary Euclidean plane). The primary plane and the secondary plane may define an angle between the primary plane and the secondary plane when lead 116 defines primary curvature and secondary curvature, such that the primary curvature and secondary curvature are out-of-plane with one another.

Lead 116 may be configured to enable transmission of stimulation signals from IMD 114 to electrode 140 and/or electrode 142 and/or sensing signals from electrode 140 and/or electrode 142 to IMD 14. Lead 116 may include an electrical conductor (not shown) configured to transmit the stimulation signals and/or sensing signals. In examples, the electrical conductor is surrounded by outer lead body 152 of lead 116. In some examples, outer lead body 152 comprises the electrical conductor. The electrical conductor may be configured to establish electrical connectivity between one or more electrodes coupled to device head 112 (e.g., electrode 140 and/or electrode 142) and processing circuitry within IMD 114. The conductor may include an insulative jacket around all or some portion of the conductor. The insulative jacket may electrically isolate the conductor from other portions of medical system 100 as well as from the environment within the patient.

In examples, the conductor is a multi-conductor comprising a plurality of conductors. The conductor may be configured such that each individual conductor in the plurality of conductors is electrically connected to an individual electrode (e.g., shallow electrode 140 or deep electrode 142) in a plurality of electrodes coupled to device head 112, IMD 114, and/or lead 116. The conductor may be configured such that each individual conductor is electrically connected to processing and/or sensing circuitry within IMD 114. The individual conductor may be configured to conduct respective signals between circuitry of IMD 114 and individual electrodes. Hence, medical system 100 may be configured to, for example, provide multi-point stimulation to tissue at or in the vicinity of a target site in a patient (e.g., target site 32 (FIGS. 1-3)).

IMD 114 may be configured to reside substantially within a vena cava of heart 26 (e.g., the IVC) when device head 112 and portions of lead 116 reside substantially within an atrium of heart 26 (e.g., the RA). IMD 114 may include a housing 154 ("IMD housing 154"). One or more portions of IMD housing 154 may define IMD distal end 115 and IMD proximal end 117. Medical system 100 may include one or more return electrodes such as return electrode 156 and return electrode 157 configured to deliver sensing/therapy in tandem with other electrodes of medical system 10. Return electrodes 156, 157 may be at any location on medical system 10. In examples, return electrode 156 is coupled to IMD housing 154 and configured to deliver the sensing/therapy in tandem with one or more electrodes coupled to device head 112 (e.g., shallow electrode 140 and/or deep electrode 142). In examples, IMD 154, device head 112, and/or lead 116 may include a nonconductive coating. Return electrodes 156, 157 and/or other electrodes of medical system 100 may be defined as an uncoated portion of medical system 100. For example, IMD housing 154 may include a nonconductive coating and define return electrode 156 as an uncoated portion of IMD housing 154.

IMD housing 154 may enclose processing and/or sensing circuitry (not shown) configured to deliver stimulation signals to and/or receive sensing signals from shallow electrode 140, deep electrode 142, and/or return electrode 156. The processing and/or sensing circuitry may be configured to provide electrical signals, e.g., pacing therapy, to shallow electrode 140, deep electrode 142, and/or return electrode 156. The processing and/or sensing circuitry may be configured to receive electrical signals, e.g., sensed cardiac electrical signals, from shallow electrode 140, deep electrode 142, and/or return electrode 156. IMD housing 154 may be configured to fluidly isolate the processing and/or sensing circuitry from an environment in contact with an exterior surface of IMD housing 154. In examples, IMD housing 154 is configured to hermetically seal an enclosure defined by IMD 114 and holding the processing and/or sensing circuitry. IMD housing 154 may be configured to define shapes that are easily accepted by the patient's body while minimizing patient discomfort. For example, IMD housing 154 may define a substantially cylindrical shape with cylindrical sidewalls. In other examples, IMD housing 154 may define substantially rectangular or other non-cylindrical shapes. IMD housing 154 may define shapes in which corners and edges are designed with relatively large radii, in order to present a housing having smoothly contoured exterior surfaces.

In examples, medical system 100 includes a fixation assembly (not shown) configured to assist in securing IMD 114 within a vena cava when delivery catheter 18 (FIGS. 1-2) has been proximally withdrawn. The fixation assembly may be coupled to IMD 114 (e.g., IMD housing 154) or some other portion of medical system 100. The fixation assembly may be configured to assume a delivery configuration when medical system 100 resides within lumen 20 of delivery catheter 18 and a deployment configuration when medical system 100 is outside of lumen 20 (e.g., when delivery catheter 18 has been proximally withdrawn). In examples, the fixation assembly is configured to expand (e.g., radially expand) when transitioning from the delivery configuration to the deployment configuration. The fixation assembly may be configured to expand to cause engagement with a vessel wall, such as an interior vessel wall of a vena cava of heart 26.

The fixation assembly may be configured to translate with IMD 114 when IMD 114 translates within lumen 20 of delivery catheter 18. In some examples, the fixation assembly is configured to engage an actuation member such as a tether, with the actuation member configured to cause the fixation assembly to transition from the delivery configuration to the deployment configuration. The actuation mechanism (e.g., the tether) may be accessible from outside of the vasculature of a patient, in order to allow a clinician to operate the actuation mechanism and cause transition to the delivery configuration. For example, some portion of the actuation mechanism (e.g., a proximal end) may extend from a proximal opening of delivery catheter 18.

The fixation assembly may be configured to engage a vessel wall of a vena cava in the deployment configuration. In examples, the fixation assembly is configured such that, on operation of the actuation member (e.g., the tether), the fixation assembly establishes physical contact with the vessel wall to maintain the positional integrity of one or more portions of medical system 100 (e.g., IMD 114). The fixation assembly may be configured to engage the vessel wall in a manner minimizing obstruction to blood flow through the vena cava. The fixation assembly may be configured to substantially secure IMD 114 within a vena cava in a manner minimizing obstruction to blood flow through the vena cava. The fixation assembly may apply little more than the force that is appropriate to one or more portions of medical system 100 (e.g., IMD 114) in place without applying excessive force to the vessel wall. The fixation assembly may be constructed to apply light, but sufficient, force to the vessel wall. Such forces are at least less than those associated with the placement of vascular stents in which the objective may be to press against the vascular wall with sufficient force to provide scaffolding support for the vessel wall.

In examples, the fixation assembly is coupled to IMD housing 154. The fixation assembly may be configured to expand radially outward from IMD housing 154 to substantially secure IMD 114 within a vena cava of heart 26 when device head 112 resides within an atrium of heart 26. In examples, the fixation assembly may include one or more loops coupled to IMD housing 154 and configured to expand to engage a vessel wall of a vena cava. The loops may be formed, for example, by an elongated member biased into a curved shape to form the one or more loops. The one or more loops may be configured to expand along an axis (e.g., a major axis and/or a minor axis of an ellipse defined by the loop) when transitioning from a delivery configuration to a deployed configuration. In some examples, one or more exterior surfaces of IMD housing 154 may be sintered to promote tissue growth along the one or more exterior surfaces. Sintering the one or more exterior surfaces may reduce strain on the fixation assembly (e.g., as a result of the sintering providing some fixation force). In some examples, the fixation assembly may be configured to engage a vessel wall at one or more points around an inner periphery of the vessel wall. The fixation assembly may be configured to engage multiple points around the inner periphery in order to foster a resistance to rotation of IMD 114 around IMD axis Li, or for another reason.

Figure 5A:
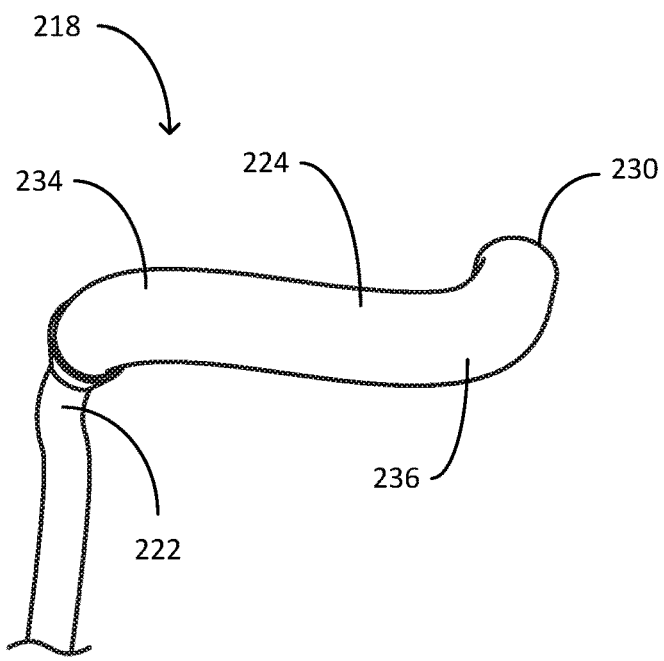
FIG. 5A is an illustration of a delivery catheter.
Figure 5B:
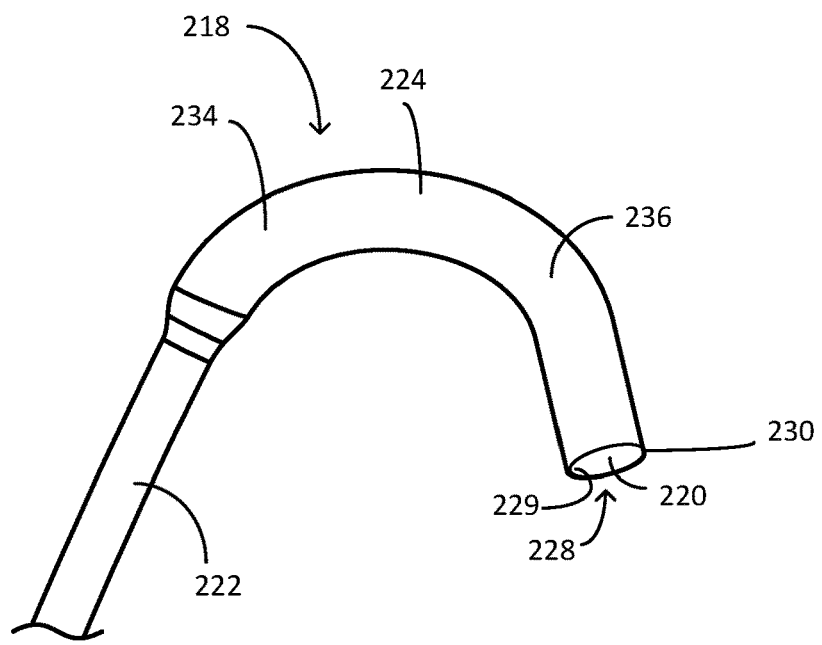
FIG. 5B is another illustration of the delivery catheter of FIG. 5A.

FIG. 5A and FIG. 5B illustrate an example delivery catheter 218 configured to deliver device head 12, 112 to a target site 32 within an atrium (e.g., the RA) of a heart 26. Delivery catheter 218 is an example of delivery catheter 18 (FIGS. 1-2). Delivery catheter 218 includes lumen 220, catheter proximal section 222, catheter distal section 224, lumen opening 228, inner wall 229, catheter distal end 230, first curvature 234, and second curvature 236, which may be configured individually and in relation to each other in the same manner as that discussed for the like-named components of delivery catheter 18.

Delivery catheter 218 may be configured to define first curvature 234 and/or second curvature 236 when medical system 10, 100 (FIGS. 1-4) is positioned within delivery catheter 218. For example, delivery catheter 218 may be configured to define first curvature 234 and/or second curvature 236 when device head 12, 112 and/or portions of lead 16, 116 are within catheter distal section 224. Delivery catheter 218 defines a lumen 220 in a manner configured to allow passage of IMD 14, 114, lead 16, 116, and device head 12, 112 therethrough. Lumen 220 extends through catheter proximal section 222 and catheter distal section 224, and opens into lumen opening 228 at catheter distal end 230. Catheter distal section 224 is configured to extend into an atrium of heart 26 (FIG. 1) as catheter proximal section 222 remains substantially within a vena cava of heart 26. Lumen 220 and lumen opening 228 are sized to allow passage of device head 12, 112, lead 16, 116, and IMD 14, 114 therethrough. Hence, delivery catheter 218 may be utilized to define a path using lumen 220 from a vena cava to a target site in an atrium for the positioning of medical system 10 within the atrium. Delivery catheter 218 is configured to be proximally withdrawn and to straighten to cause medical system 10 to pass through lumen opening 228.

Delivery catheter 218 is illustrated in a substantially relaxed position, such that catheter distal section 224 is substantially free of external forces acting on catheter distal section 224. Catheter distal section 224 is configured to define first curvature 234 and second curvature 236 in the substantially relaxed position. Catheter distal section 224 may be configured to define first curvature 234 out of plane with the second curvature 236 in order to, for example, cause lumen 220 to define a path from a vena cave to a target site within an atrium.

Figure 6A:
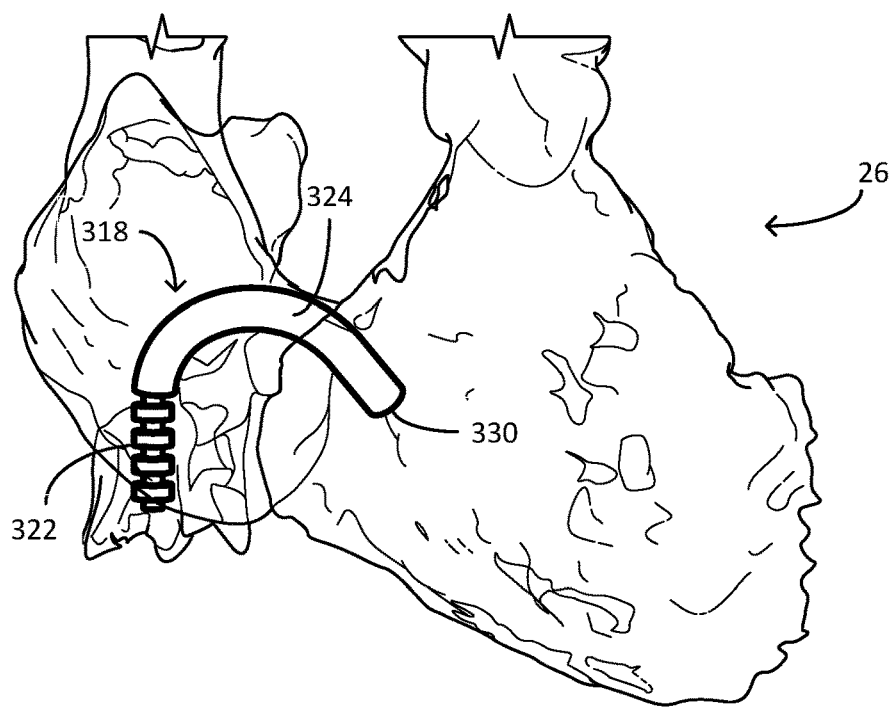
FIG. 6A is an illustration of a delivery catheter within a heart.
Figure 6B:
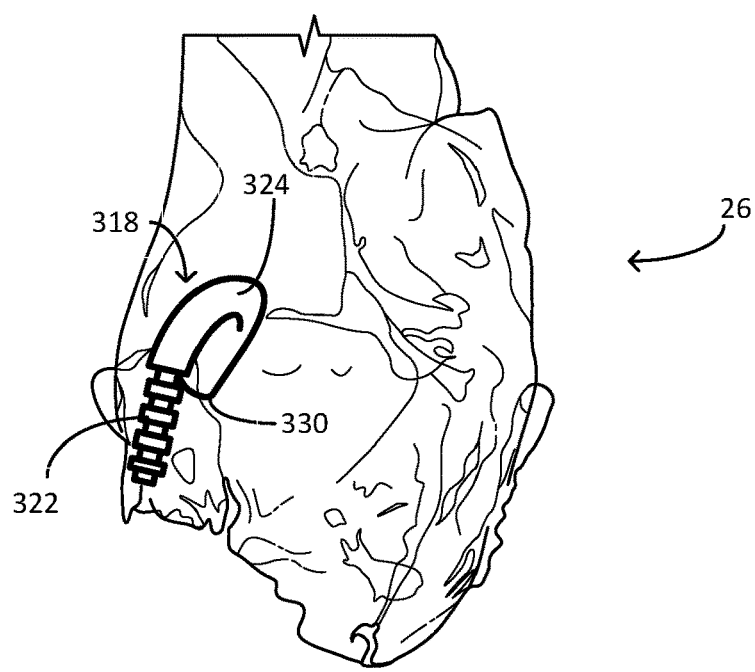
FIG. 6B is another illustration of the delivery catheter of FIG. 6A within the heart.

FIG. 6A and FIG. 6B illustrate an example delivery catheter 318 defining a pathway from a vena cava of heart 26 to an atrium of heart 26 using a lumen (e.g., lumen 20, 220) defined by delivery catheter 318. Heart 26 is illustrated as transparent with delivery catheter 318 positioned inside heart 26 in FIG. 6A and FIG. 6B. Delivery catheter 318 includes catheter proximal section 322, catheter distal section 324, and catheter distal end 330, which may be configured individually and relation to each other in the same manner as that discussed for the like-named components of delivery catheter 18 and/or delivery catheter 218. Delivery catheter 318 is an example of delivery catheter 18 and/or delivery catheter 218.

In FIG. 6A and FIG. 6B, delivery catheter 318 is positioned such that catheter proximal section 322 is substantially within the vena cava of heart 26 and catheter distal section 324 is substantially within the atrium of heart 26. FIG. 6A provides an anteroposterior (AP) view and FIG. 6B provides a view rotated 90 degrees from the AP view. Delivery catheter 318 (e.g., catheter distal section 324 and catheter proximal section 322) may be inserted intravenously through the vena cava to cause catheter distal section 324 to enter the atrium. Delivery catheter 318 may be configured to define first curvature 34, 234 and/or second curvature 36, 236 as catheter distal section 324 enters the atrium, and may be configured to define first curvature 34, 234 and/or second curvature 36, 236 when catheter distal section 324 resides within the atrium.

Figure 7:
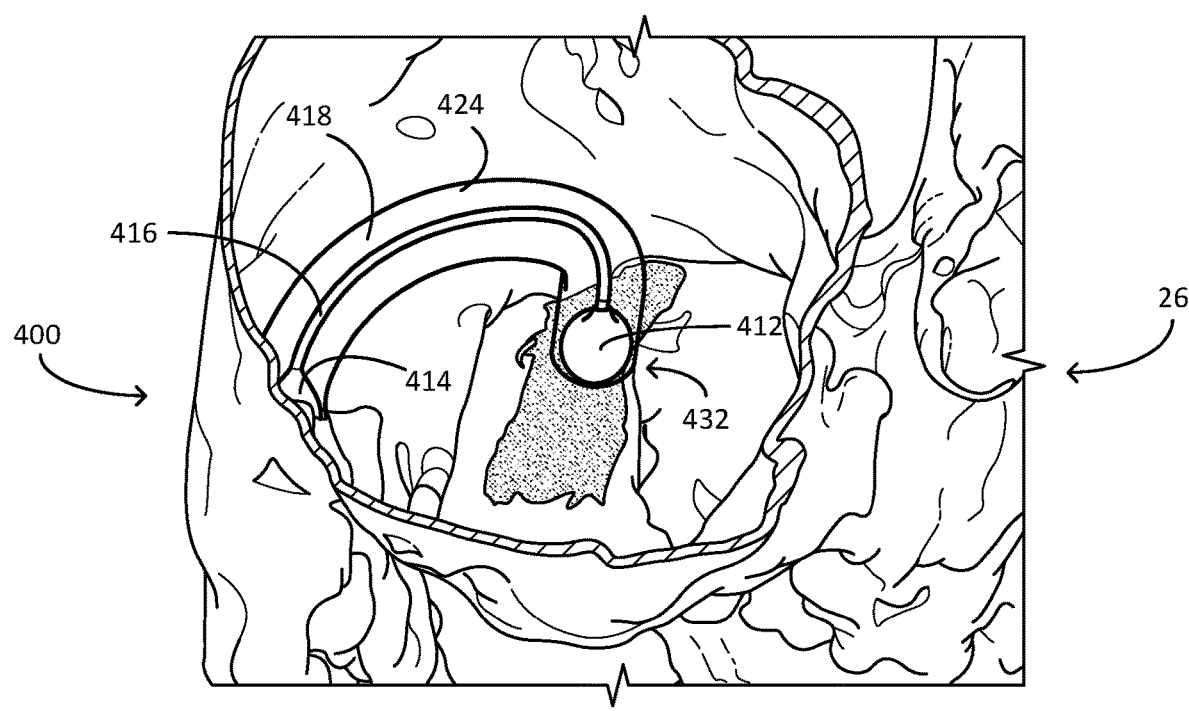
FIG. 7 is an illustration of a medical system and delivery catheter within a heart.

FIG. 7 illustrates a delivery catheter 418 including catheter distal section 424. Delivery catheter 418 is an example of delivery catheter 18, delivery catheter 218, and/or delivery catheter 318. Delivery catheter 418 includes a lumen defining a pathway from a vena cava of heart 26 to an atrium of heart 26. A medical system 400 including device head 412, lead 416, and IMD 414 is positioned within the lumen of delivery catheter 418. Medical system 400 is an example of medical system 10 and/or medical system 100. In FIG. 7, delivery catheter 418 is configured such that medical system 400 may be positioned within the lumen defined by delivery catheter 418 from a vena cava of heart 26 to an atrium of heart 26. Delivery catheter 418 is configured to substantially guide device head 412 and portions of lead 416 from the vena cava to a target site 432 within the atrium. Device head 412, lead 416, and IMD 414 may be configured individually and relation to each other in the same manner as that discussed for the like-named components of medical system 10 and/or medical system 100.

Figure 8A:
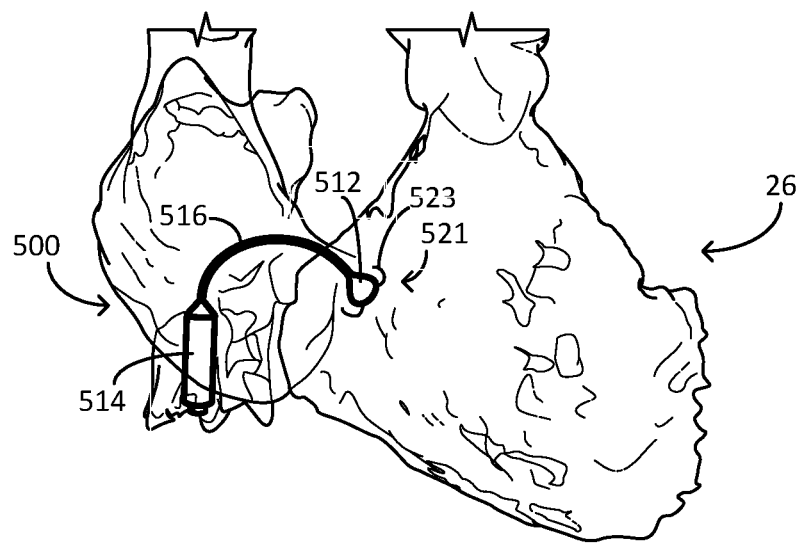
FIG. 8A is an illustration of a medical system implanted within a heart.
Figure 8B:
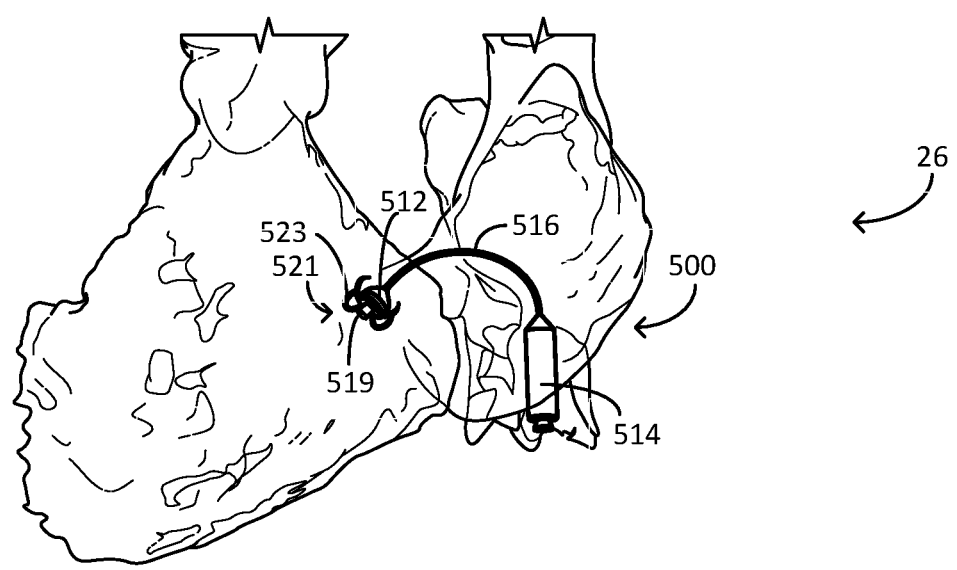
FIG. 8B is another illustration of the medical system of FIG. 8A.
Figure 8C:
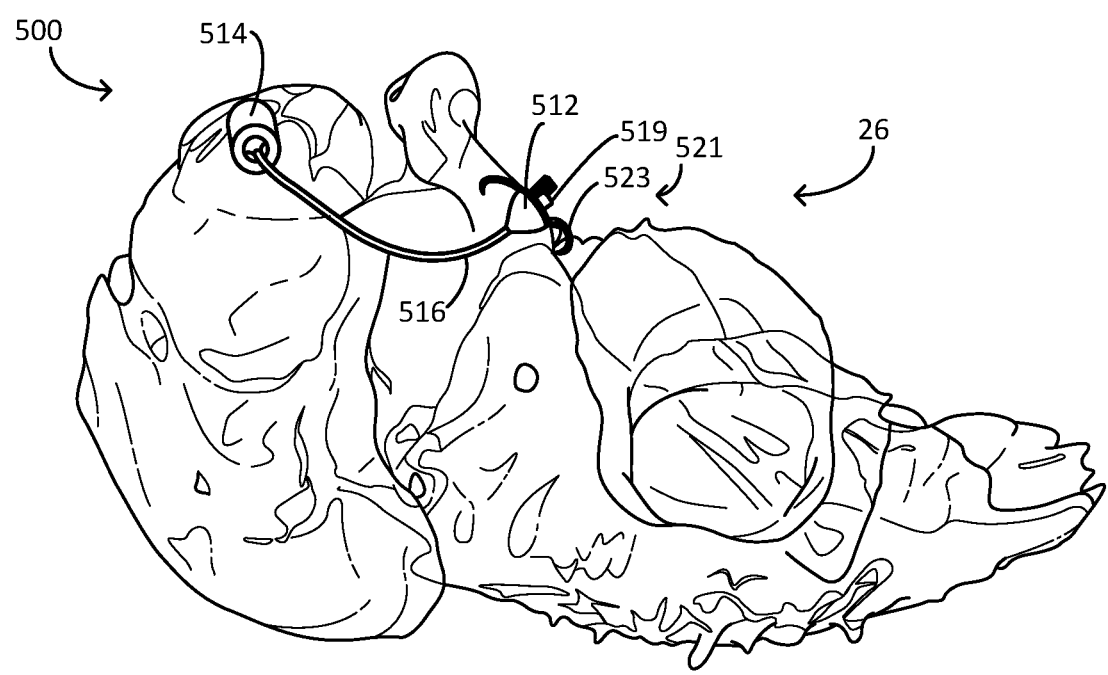
FIG. 8C is a further illustration of the medical system of FIG. 8A and FIG. 8B.

FIG. 8A, FIG. 8B, and FIG. 8C illustrate an example medical system 500 implanted within a heart 26. Medical system 500 is an example of medical system 10, medical system 100, and/or medical system 400. Heart 26 is illustrated as transparent with medical system 500 positioned inside heart 26 in FIG. 8A, FIG. 8B, and FIG. 8C. Medical system 500 includes device head 512, lead 516, IMD 514, electrode 519, and fixation element 521 including fixation tine 523, all of which may be configured individually and relation to each other in the same manner as that discussed for the like-named components of medical system 10, medical system 100, and/or medical system 400. Fixation element 521 is engaged with (e.g., grasping) tissues within a target site 532 and substantially maintaining device head 512 within an atrium of heart 26. Lead 516 extends between device head 512 to IMD 514. IMD 514 is positioned substantially within a vena cava of heart 26. FIG. 8A provides an anteroposterior (AP) view and FIG. 8B provides a posteroanterior (PA) view. FIG. 8C provides a top view.

Figure 9:
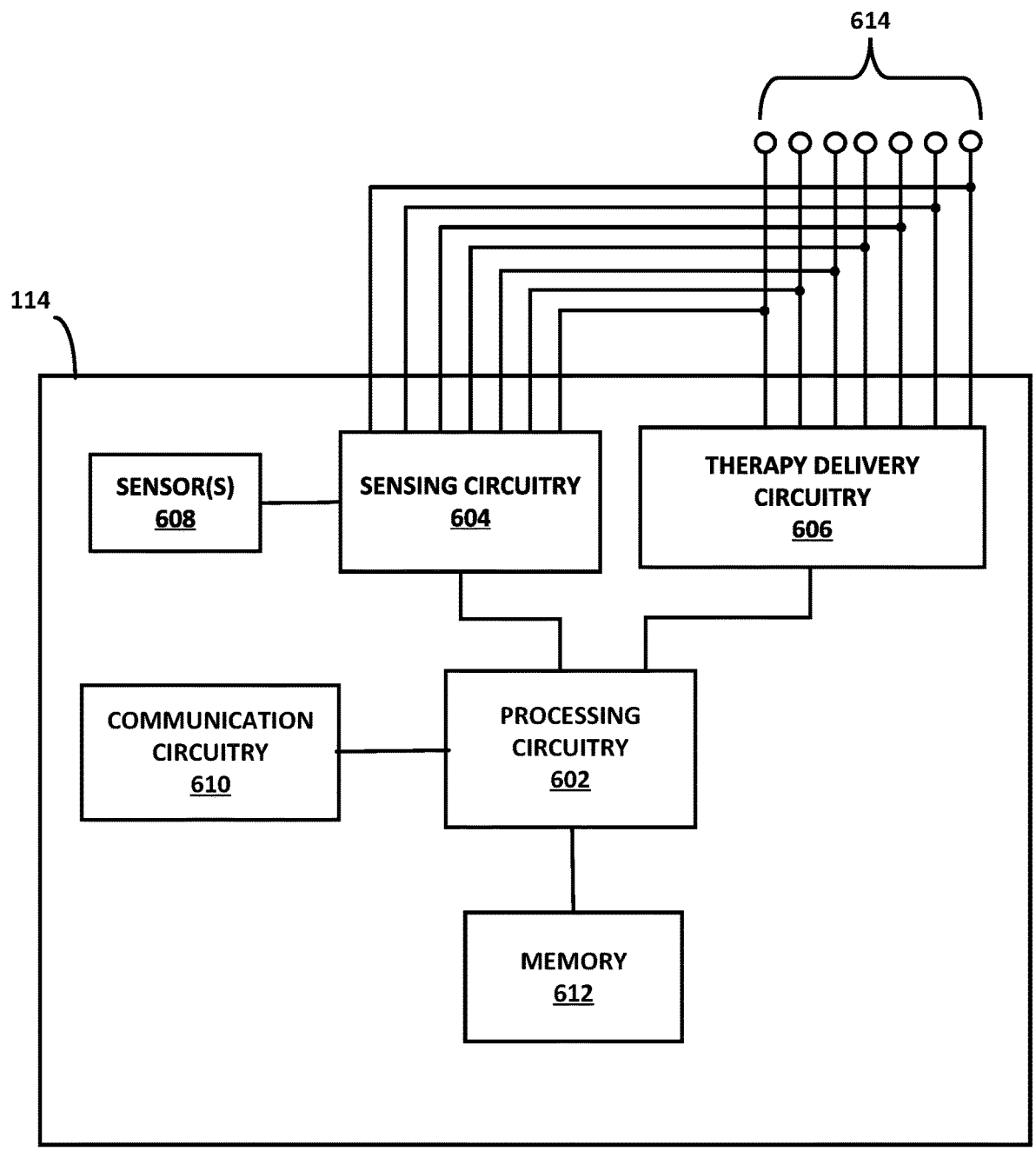
FIG. 9 is a schematic illustration of an implantable medical device.

FIG. 9 is a functional block diagram illustrating an example configuration of IMD 14, 114, 414, 514. As shown in FIG. 9, IMD 14, 114, 414, 514 includes processing circuitry 602, sensing circuitry 604, therapy delivery circuitry 606, sensors 608, communication circuitry 610, and memory 612. In some examples, memory 612 includes computer-readable instructions that, when executed by processing circuitry 602, cause IMD 14, 114, 414, 514 and processing circuitry 602 to perform various functions attributed to IMD 14, 114, 414, 514 and processing circuitry 602 herein. Memory 612 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 602 may include fixed function circuitry and/or programmable processing circuitry. Processing circuitry 602 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 602 may include multiple components, such as any combination of one or more microprocessors, one or more controllers, one or more DSPs, one or more ASICs, or one or more FPGAs, as well as other discrete or integrated logic circuitry. The functions attributed to processing circuitry 602 herein may be embodied as software, firmware, hardware or any combination thereof.

In some examples, processing circuitry 602 may receive (e.g., from an external device), via communication circuitry 610, a respective value for each of a plurality of cardiac sensing parameters, cardiac therapy parameters (e.g., cardiac pacing parameters), and/or electrode vectors. Processing circuitry 602 may store such parameters and/or electrode vectors in memory 612.

Therapy delivery circuitry 606 and sensing circuitry 604 are electrically coupled to electrodes 614, which may correspond to electrode 19, 519, shallow electrode 140 and/or deep electrode 142. Processing circuitry 602 is configured to control therapy delivery circuitry 606 to generate and deliver electrical therapy to heart 26 via electrodes 614. Electrical therapy may include, for example, pacing pulses, or any other suitable electrical stimulation. Processing circuitry 602 may control therapy delivery circuitry 606 to deliver electrical stimulation therapy via electrodes 614 according to one or more therapy parameter values, which may be stored in memory 612. Therapy delivery circuitry 606 may include capacitors, current sources, and/or regulators, in some examples.

In addition, processing circuitry 602 is configured to control sensing circuitry 604 to monitor signals from electrodes 614 in order to monitor electrical activity of heart 26. Sensing circuitry 604 may include circuits that acquire electrical signals, such as filters, amplifiers, and analog-to-digital circuitry. Electrical signals acquired by sensing circuitry 604 may include intrinsic and/or paced cardiac electrical activity, such as atrial depolarizations and/or ventricular depolarizations. Sensing circuitry 604 may filter, amplify, and digitize the acquired electrical signals to generate raw digital data. Processing circuitry 602 may receive the digitized data generated by sensing circuitry 604. In some examples, processing circuitry 602 may perform various digital signal processing operations on the raw data, such as digital filtering. In some examples, in addition to sensing circuitry 604, IMD 14, 114, 414, 514 optionally may include sensors 608, which may be one or more pressure sensors and/or one or more accelerometers, as examples. Communication circuitry 610 may include any suitable hardware (e.g., an antenna), firmware, software, or any combination thereof for communicating with another device, e.g., external to the patient.

Figure 10:
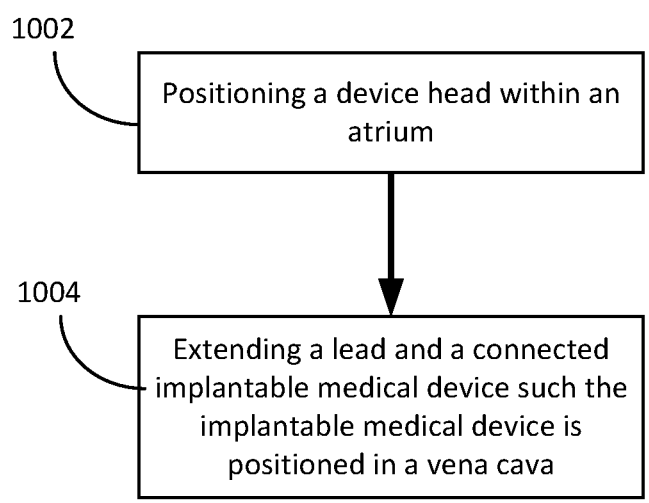
FIG. 10 illustrates an example technique for positioning a medical system within a heart.

A technique for positioning a medical system 100 within an atrium of a heart is illustrated in FIG. 10. Although the technique is described mainly with reference to medical system 10 and delivery catheter 18 of FIGS. 1-3, the technique may be applied to other medical systems in other examples, including medical systems 100, 400, 500 and delivery catheter 218, 318, 418.

The technique includes positioning a device head 12 of medical system 10 within an atrium of a heart 26 by transmitting an axial force to device head 12 (1002). The technique may include positioning the device head 12 at a target site 32 within the atrium. The technique may include extending lead 16 from device head 12 to an IMD 14 within a vena cava of heart 26 (1004). The technique may include delivering sensing/therapy signals to tissues within target site 32 using an electrode 19 coupled to device head 12. Electrode 19 may receive stimulation signals from IMD 14 and deliver the sensing/therapy signals to the tissue based on the stimulation signals. In examples, the technique includes sending the stimulation signals from processing circuitry within IMD 14 to electrode 19.

In examples, the technique includes defining a pathway from the vena cava of heart 26 to target site 32 within the atrium of heart 26 using delivery catheter 18. The technique may include translating delivery catheter 18 through the vena cava and causing some portion of delivery catheter 18 to enter the atrium. In examples, the technique includes causing catheter distal section 24 to enter the atrium. The technique may include defining a first curvature 34 and/or second curvature 36 using catheter distal section 24 when catheter distal section 24 positions or is positioned within the atrium. In examples, the technique includes positioning a distal end 30 of delivery catheter 18 in the vicinity of target site 32 using the first curvature 34 and/or the second curvature 36. The technique may include defining the pathway from the vena cava to target site 32 using a lumen 20 defined by delivery catheter 18

The technique may include positioning medical system 10 within the atrium of heart 26 when delivery catheter 18 enters the atrium. The technique may include translating medical system 10 through lumen 20 to cause device head 12 to position within the atrium of heart 26. In some examples, the technique includes causing medical system 10 to translate by exerting a distal or proximal force on IMD 14 (e.g., on IMD proximal end 17). The technique may include transmitting some portion of the force on IMD 14 through lead 16 to device head 12. The technique may include causing device head 12 to translate using the portion of the force transmitted through lead 16. In some examples, the technique includes causing medical system 10 to translate by exerting a distal or proximal force on device head 12 (e.g., on head first side 11). The technique may include transmitting some portion of the force on device head 12 through lead 16 to IMD 14. The technique may include causing IMD 14 to translate using the portion of the force transmitted through lead 16. The technique may include using stylet 38 to impart a force on IMD 14 and/or device head 12.

In examples, the technique includes translating device head 12 and at least some portion of lead 16 through a portion of lumen 20 within catheter distal section 24. The technique may include translating device head 12 toward a lumen opening 28 at catheter distal end 30 of delivery catheter 18. In examples, the technique include using delivery catheter 18 to substantially resist a rotation of device head 12 as device head 12 translates toward lumen opening 28. The technique may include using delivery catheter 18 to cause a head second side 13 to remain distal to a head first side 11 opposite head second side 13 as device head 12 translates toward lumen opening 28.

The technique may include translating a fixation element 21 coupled to device head 12 distally through lumen opening 28 as device head 12 translates toward lumen opening 28. The technique may include causing fixation element 21 to engage tissues within target site 32 by translating fixation element 21 through lumen opening 28. In examples, the technique includes extending fixation element 21 distally from head second side 13. In examples, the technique includes causing a free end (e.g., free end 148 (FIG. 4) of a fixation tine 23 to penetrate tissues within target site 32. The technique may include causing fixation tine 23 to expand radially outward as fixation element 21 translates through lumen opening 28.

The technique may include causing electrode 19 on device head 12 (e.g., on head second side 13) to contact tissues within target site 32 by translating device head 12 through lumen opening 28. The technique may include causing electrode 19 to contact the tissues using fixation element 21. The technique may include substantially securing device head 12 within the atrium of heart 26 using fixation element 21. The technique may include substantially securing device head 12 within the atrium (e.g., the RA) of heart 26 while IMD 14 is positioned within the vena cava (e.g., the IVC) of heart 26.

The technique may include causing medical system 10 to translate through lumen opening 28 by proximally withdrawing delivery catheter 18. The technique may include substantially retaining device head 12 within the atrium using fixation element 21 and substantially retaining IMD 14 within the vena cava by proximally withdrawing delivery catheter 18.

The disclosure includes the following examples.

Example 1: A medical system comprising: an implantable medical device having a proximal end and a distal end, wherein the implantable medical device is configured to be positioned within a vena cava of a heart; a flexible lead, wherein a proximal end of the flexible lead is attached to the distal end of the implantable medical device, wherein the flexible lead is configured to extend from the vena cava to an atrium of a heart; a device head, wherein a first side of the device head is attached to a distal end of the flexible lead, wherein the device head is configured to be positioned within the atrium of the heart; a fixation element attached to the device head, wherein the fixation element is configured to engage tissue to substantially secure the device head within the atrium of the heart; and an electrode coupled to the device head, wherein the electrode is configured to provide stimulation to tissues of the heart when the device head is positioned within the atrium of the heart.

Example 2: The medical system of example 1, wherein the electrode is electrically connected to circuitry within the implantable medical device.

Example 3: The medical system of example 1 or example 2, wherein the electrode is coupled to a second side of the device head opposite the first side.

Example 4: The medical system of any of examples 1-3, wherein the fixation element comprises one or more fixation tines attached to the device head, wherein the one or more fixation tines are configured to extend distally from the device head.

Example 5: The medical system of any of examples 1-4, wherein the flexible lead defines an axis from the proximal end of the flexible lead to the distal end of the flexible lead, and wherein the flexible lead is configured to transmit a force along the axis from the implantable medical device or the device head to the other of the implantable medical device or the device head.

Example 6: The medical system of example 5, wherein the flexible lead is configured to have an axial stiffness relative to the axis greater than a bending stiffness relative to the axis.

Example 7: The medical system of any of examples 1-6, wherein the electrode is configured to engage a wall of the atrium via non-invasive physical contact when the device is positioned within the atrium.

Example 8: The medical system of any of examples 1-7, further comprising an electrode support member, wherein a proximal end of the electrode support member is attached to the second side of the device head and the electrode is located at a distal end of the electrode support member.

Example 9: The medical system of example 8, wherein the electrode support member is configured to advance the electrode into a tissue wall of the atrium by piercing the tissue wall of the atrium when the device is positioned within the atrium.

Example 10: The medical system of example 9, wherein the electrode support member is configured to advance the electrode into ventricular tissue of the heart.

Example 11: The medical system of any of examples 1-10, further comprising a stylet having a proximal end and a distal end, wherein the stylet is configured to impart an axial force in a distal direction to the device head, and wherein the first side of the device head is configured to receive the axial force from the distal end of the stylet.

Example 12: The medical system of any of examples 1-11, further comprising a device fixation element coupled to the implantable medical device, wherein the device fixation element is configured to position the implantable medical device within the vena cava of the heart.

Example 13: The medical system of any of examples 1-12, wherein the fixation member includes one or more fixation tines, wherein an individual fixation tine in the one or more fixation tines comprises a fixed end attached to the device head and a free end opposite the fixed end, and wherein the individual fixation tine is resiliently biased to pivot the free end radially outward from a longitudinal axis defined by the device head.

Example 14: The medical system of example 13, wherein the individual fixation tine includes a midpoint between the fixed end and the free end, wherein the individual fixation tine is resiliently biased to establish a configuration wherein the midpoint is distal to the free end and distal to the fixed end.

Example 15: The medical system of any of examples 1-14, wherein the fixation member includes a plurality of fixation tines, wherein each fixation tine in the plurality of fixation tines comprises a fixed end attached to the device head and a free end opposite the fixed end, such that the plurality of fixation tines comprise a plurality of fixed ends, and wherein the plurality of fixed ends surround the electrode.

Example 16: The medical system of any of examples 1-15, further comprising a delivery catheter defining a lumen, wherein: the lumen is configured to surround at least the implantable medical device, the flexible lead, the device head, and the fixation element; the lumen defines a lumen axis; and the implantable medical device, the flexible lead, the device head, and the fixation element are slidable along the lumen axis.

Example 17: The medical system of example 16, wherein the delivery catheter includes a proximal section and a distal section, wherein the distal portion includes a shape-memory alloy configured to define a curvature.

Example 18: The medical system of example 17, wherein the proximal portion is configured to at least partially reside within the vena cava when the distal section at least partially resides in the atrium.

Example 19: The medical system of example 17 or example 18, wherein the shape-memory alloy is configured to define a first curvature and a second curvature, wherein the second curvature is out-of-plane with the first curvature.

Example 20: The medical system of any of examples 17-19, wherein the proximal portion is configured to surround the implantable medical device when the distal portion surrounds the device head and the fixation element.

Example 21: The medical system of any of examples 17-20, wherein the delivery catheter defines a lumen opening at a distal end of the delivery catheter, and wherein the fixation element, the device head, the flexible lead, and the implantable medical device are configured to pass therethrough.

Example 22: The medical system of example 22, wherein the fixation element comprises one or more fixation tines, wherein the one or more fixation tines are configured to expand radially outward when the delivery catheter is proximally withdrawn from a first position wherein the one or more fixation tines are proximal to the lumen opening to second position wherein the one or more fixation tines are distal to the lumen opening.

Example 23: The medical system of any of examples 1-22, wherein the flexible lead is configured to position the implantable medical device within the vena cava of the heart when the fixation element substantially secures the device head within the atrium of the heart.

Example 24: A system comprising: a medical assembly comprising: an implantable medical device having a proximal end and a distal end, wherein the implantable medical device is configured to be positioned within a vena cava of a heart; a flexible lead, wherein a proximal end of the flexible lead is attached to the distal end of the implantable medical device, wherein the flexible lead is configured to extend from the vena cava to an atrium of a heart; a device head, wherein a first side of the device head is attached to a distal end of the flexible lead, wherein the device head is configured to be positioned within the atrium of the heart; a fixation element attached to the device head, wherein the fixation element is configured to engage tissue to substantially secure the device head within the atrium of the heart; and an electrode coupled to the device head, wherein the electrode is configured to provide stimulation to tissues of the heart when the device head is positioned within the atrium of the heart; and a delivery catheter defining a lumen and defining a lumen opening at a distal end of the delivery catheter, wherein: the lumen is configured to surround at least the implantable medical device, the flexible lead, the device head, and the fixation element, and the fixation element, the device head, the flexible lead, and the implantable medical device are configured to pass distally through the lumen opening.

Example 25: The medical system of example 24, wherein the flexible lead defines an axis from the proximal end of the flexible lead to the distal end of the flexible lead, and wherein the flexible lead is configured to transmit a force along the axis from the implantable medical device or the device head to the other of the implantable medical device or the device head.

Example 26: The medical system of example 24 or example 25, wherein the fixation element comprises one or more fixation tines attached to the device head, wherein the one or more fixation tines are configured to extend distally from the device head.

Example 27: The medical system of any of examples 24-26, wherein the delivery catheter includes a proximal portion and a distal portion, wherein the distal portion includes a shape-memory alloy configured to define a curvature.

Example 28: The medical system of example 27, wherein the delivery catheter is configured to reduce the curvature when the delivery catheter is proximally withdrawn to cause one or more portions of the medical assembly to pass through the lumen opening.

Example 29: The medical system of example 28, wherein the proximal portion is configured to at least partially reside within the vena cava when the distal section at least partially resides in the atrium.

Example 30: The medical system of any of examples 27-29, wherein the shape-memory alloy is configured to define a first curvature and a second curvature, wherein the second curvature is out-of-plane with the first curvature.

Example 31: A method comprising: positioning a device head, an electrode attached to the device head, and a fixation element attached to the device head within an atrium of a heart by transmitting an axial force to the device head; causing a flexible lead attached to the device head and attached to an implantable medical device to extend from the atrium of the heart to a vena cava of the heart using the transmitted axial force; and positioning the implantable medical device within the vena cava of the heart using the transmitted axial force.

Example 32: The method of example 31, further comprising translating the device head, the electrode, the fixation element, the flexible lead, and the implantable medical device through a delivery catheter.

Example 33: The method of examples 31 or example 32, further comprising positioning a proximal portion of the delivery catheter in the vena cava and positioning a distal portion of the delivery catheter in the atrium.

Example 34: The method of example 33, further comprising defining a curvature in the distal portion of the delivery catheter when the distal portion of the catheter is positioned in the atrium.

Example 35: The method of example 34, further comprising causing the delivery catheter to reduce the curvature by proximally withdrawing the delivery catheter to cause at least one of the device head, the lead, or the implantable medical device to pass through a lumen opening of the delivery catheter.

Example 36: The method of any of examples 31-35, further comprising exerting the axial force on the implantable medical device and transmitting some portion of the axial force to the device head using the flexible lead.

Example 37: The method of any of examples 31-36, further comprising exerting the axial force on the device head using an elongated member and transmitting some portion of the axial force to the implantable medical device using the flexible lead.

Example 38: The method of any of examples 31-37, further comprising causing the fixation element to engage a wall of the atrium when the device head, the electrode, and the fixation element attached are positioned within the atrium.

Various examples of the disclosure have been described. Any combination of the described systems, operations, or functions is contemplated. These and other examples are within the scope of the following claims.

What is claimed is:

1. A medical system comprising:
   an implantable medical device having a proximal end and a distal end, wherein the implantable medical device is configured to be positioned within a vena cava of a heart;
   a flexible lead, wherein a proximal end of the flexible lead is attached to the distal end of the implantable medical device, wherein the flexible lead is configured to extend from the vena cava to a chamber of the heart, wherein the flexible lead defines an axis from the proximal end of the flexible lead to a distal end of the flexible lead, and wherein the flexible lead is configured to have an axial stiffness relative to the axis greater than a bending stiffness relative to the axis;
   a device head, wherein a first side of the device head is attached to the distal end of the flexible lead, wherein the device head is configured to be positioned within the chamber of the heart, and wherein the flexible lead is configured to transmit a force along the axis from one of the implantable medical device or the device head to the other of the implantable medical device or the device head;
   a fixation element attached to the device head, wherein the fixation element is configured to engage tissue to substantially secure the device head within the chamber of the heart; and
   an electrode coupled to the device head, wherein the electrode is configured to provide stimulation to tissues of the heart when the device head is positioned within the chamber of the heart.

2. The medical system of claim 1, wherein the electrode is electrically connected to circuitry within the implantable medical device.

3. The medical system of claim 1, wherein the electrode is coupled to a second side of the device head opposite the first side.

4. The medical system of claim 1, wherein the fixation element comprises one or more fixation tines attached to the device head, wherein the one or more fixation tines are configured to extend distally from the device head.

5. The medical system of any one of claims 1-4, wherein the device head is configured to receive a distal end of a stylet, wherein the device head is configured to receive an axial force in a distal direction imparted by the stylet when the device head receives the distal end of the stylet.

6. The medical system of claim 1, wherein the flexible lead is configured to position the implantable medical device within the vena cava of the heart when the fixation element substantially secures the device head within the chamber of the heart.

7. The medical system of claim 1, wherein the fixation member includes one or more fixation tines, wherein an individual fixation tine in the one or more fixation tines comprises a fixed end attached to the device head and a free end opposite the fixed end.

8. The medical system of claim 7, wherein the individual fixation tine is resiliently biased to pivot the free end radially outward from a longitudinal axis defined by the device head.

9. The medical system of claim 1, further comprising a delivery catheter defining a lumen, wherein:
   the lumen is configured to surround at least the implantable medical device, the flexible lead, the device head, and the fixation element;
   the lumen defines a lumen axis; and
   the implantable medical device, the flexible lead, the device head, and the fixation element are slidable along the lumen axis.

10. The medical system of claim 9, wherein the delivery catheter includes a proximal section and a distal section, wherein the distal portion includes a shape-memory alloy configured to define a curvature.

11. The medical system of claim 10, wherein the shape-memory alloy is configured to define a first curvature and a second curvature, wherein the second curvature is out-of-plane with the first curvature.

12. The medical system of claim 9, wherein the delivery catheter defines a lumen opening at a distal end of the delivery catheter, and wherein the fixation element, the device head, the flexible lead, and the implantable medical device are configured to pass therethrough.

13. The medical system of claim 12, wherein the fixation element comprises one or more fixation tines, wherein the one or more fixation tines are configured to expand radially outward when the delivery catheter is proximally withdrawn from a first position wherein the one or more fixation tines are proximal to the lumen opening to a second position wherein the one or more fixation tines are distal to the lumen opening.

14. A system comprising:
   a medical assembly comprising:
      an implantable medical device having a proximal end and a distal end, wherein the implantable medical device is configured to be positioned within a vena cava of a heart;
      a flexible lead, wherein a proximal end of the flexible lead is attached to the distal end of the implantable medical device, wherein the flexible lead is configured to extend from the vena cava to an atrium of the heart, wherein the flexible lead defines an axis from the proximal end of the flexible lead to a distal end of the flexible lead, and wherein the flexible lead is configured to have an axial stiffness relative to the axis greater than a bending stiffness relative to the axis;
      a device head, wherein a first side of the device head is attached to the distal end of the flexible lead, wherein the device head is configured to be positioned within the atrium of the heart, wherein the flexible lead is configured to transmit a force along the axis from one of the implantable medical device or the device head to the other of the implantable medical device or the device head;

a fixation element attached to the device head, wherein the fixation element is configured to engage tissue to substantially secure the device head within the atrium of the heart; and an electrode coupled to the device head, wherein the electrode is configured to provide stimulation to tissues of the heart when the device head is positioned within the atrium of the heart; and a delivery catheter defining a lumen and defining a lumen opening at a distal end of the delivery catheter, wherein:

the lumen is configured to surround at least the implantable medical device, the flexible lead, the device head, and the fixation element, and the fixation element, the device head, the flexible lead, and the implantable medical device are configured to pass distally through the lumen opening.

15. The medical system of claim 14, wherein the delivery catheter includes a proximal portion and a distal portion, wherein the distal portion includes a shape-memory alloy configured to define a first curvature and a second curvature, wherein the second curvature is out-of-plane with the first curvature.

16. The medical system of claim 14, wherein the flexible lead is configured to position the implantable medical device within the vena cava of the heart when the fixation element substantially secures the device head within the atrium of the heart.

17. A method comprising:

positioning a device head, an electrode attached to the device head, and a fixation element attached to the device head within a chamber of a heart by transmitting an axial force to the device head, wherein a first side of the device head is attached to the a distal end of a flexible lead, wherein the electrode is configured to provide stimulation to tissues of the heart when the device head is positioned within the chamber of the heart, and wherein the fixation element is configured to engage tissue to substantially secure the device head within the chamber of the heart;

causing the flexible lead attached to the device head and attached to an implantable medical device to extend from the chamber of the heart to a vena cava of the heart using the transmitted axial force, wherein a proximal end of the flexible lead is attached to a distal end of the implantable medical device, wherein the flexible lead defines an axis from the proximal end of the flexible lead to the distal end of the flexible lead, wherein the flexible lead is configured to have an axial stiffness relative to the axis greater than a bending stiffness relative to the axis, and wherein the flexible lead is configured to transmit the axial force along the axis from one of the implantable medical device or the device head to the other of the implantable medical device or the device head; and positioning the implantable medical device within the vena cava of the heart using the transmitted axial force.

18. The method of claim 17 further comprising translating the device head, the electrode, the fixation element, the flexible lead, and the implantable medical device through a delivery catheter.

* * * * *